US008642067B2

(12) United States Patent
Trogden et al.

(10) Patent No.: US 8,642,067 B2
(45) Date of Patent: Feb. 4, 2014

(54) METHODS AND COMPOSITIONS FOR INTRAOCULAR ADMINISTRATION TO TREAT OCULAR CONDITIONS

(75) Inventors: John T. Trogden, Anaheim, CA (US); Robert T. Lyons, Laguna Hills, CA (US); James N. Chang, Newport Beach, CA (US); Scott M. Whitcup, Laguna Hills, CA (US)

(73) Assignee: Allergen, Inc., Irvine, CA (US)

( * ) Notice: Subject to any disclaimer, the term of this patent is extended or adjusted under 35 U.S.C. 154(b) by 1676 days.

(21) Appl. No.: 11/695,527

(22) Filed: Apr. 2, 2007

(65) Prior Publication Data

US 2008/0241252 A1 Oct. 2, 2008

(51) Int. Cl.
*A61F 2/00* (2006.01)
(52) U.S. Cl.
USPC .......................................... 424/428
(58) Field of Classification Search
USPC .......................................... 424/428
See application file for complete search history.

(56) References Cited

U.S. PATENT DOCUMENTS

| | | | |
|---|---|---|---|
| 4,327,725 A | 5/1982 | Cortese |
| 4,474,451 A | 10/1984 | Mizokami |
| 5,166,331 A | 11/1992 | Della Valle et al. |
| 5,580,979 A | 12/1996 | Bachovchin |
| 5,674,892 A | 10/1997 | Giese |
| 5,700,822 A | 12/1997 | Hirth |
| 5,721,277 A | 2/1998 | Tang |
| 5,728,726 A | 3/1998 | Giese |
| 5,760,066 A | 6/1998 | Tang |
| 5,776,902 A | 7/1998 | Bachovchin |
| 5,795,910 A | 8/1998 | Giese |
| 5,914,343 A | 6/1999 | Tang |
| 5,919,813 A | 7/1999 | DeJuan |
| 5,958,959 A | 9/1999 | Hirth |
| 5,980,929 A | 11/1999 | DeJuan |
| 5,990,141 A | 11/1999 | Hirth |
| 6,028,099 A | 2/2000 | DeJuan |
| 6,071,332 A | 6/2000 | Schulz |
| 6,331,555 B1 | 12/2001 | Hirth |
| 6,344,455 B1 | 2/2002 | Bridges |
| 6,395,734 B1 | 5/2002 | Tang |
| 6,399,655 B1 | 6/2002 | DeJuan |
| 6,451,838 B1 | 9/2002 | Moon |
| 6,465,507 B2 | 10/2002 | Tang |
| 6,482,848 B2 | 11/2002 | Moon |
| 6,514,981 B1 | 2/2003 | Tang |
| 6,531,502 B1 | 3/2003 | Tang |
| 6,559,173 B1 | 5/2003 | Andrews |
| 6,680,048 B2 | 1/2004 | Grainger |
| 6,685,938 B1 | 2/2004 | Cheresh |
| 6,689,806 B1 | 2/2004 | Tang |
| 6,699,863 B1 | 3/2004 | Andrews |
| 6,709,709 B1 | 3/2004 | Ozawa |
| 6,710,067 B2 | 3/2004 | Moon |
| 6,713,474 B2 | 3/2004 | Hirst |
| 6,716,870 B2 | 4/2004 | Moon |
| 6,767,025 B2 | 7/2004 | Hagen |
| 6,777,439 B2 | 8/2004 | Durden |
| 6,855,730 B2 | 2/2005 | Tang |
| 6,869,962 B2 | 3/2005 | Collins |
| 6,872,724 B2 | 3/2005 | Zhao |
| 6,875,767 B2 | 4/2005 | Bilodeau |
| 6,878,714 B2 | 4/2005 | Askew |
| 6,906,093 B2 | 6/2005 | Tang |
| 6,927,293 B2 | 8/2005 | Kim |
| 6,933,299 B1 | 8/2005 | Cockerill |
| 6,979,675 B2 | 12/2005 | Tidmarsh |
| 6,995,162 B2 | 2/2006 | Chen |
| 7,005,444 B2 | 2/2006 | Andrews |
| 7,008,943 B2 | 3/2006 | Moon |
| 7,015,220 B2 | 3/2006 | Andrews |
| 7,037,498 B2 | 5/2006 | Cohen |
| 7,045,528 B2 | 5/2006 | Collins |
| 7,053,113 B2 | 5/2006 | Moon |
| 7,091,181 B2 | 8/2006 | Demopulos |
| 7,098,236 B2 | 8/2006 | Andrews |
| 7,101,884 B2 | 9/2006 | Arrington |
| 7,105,531 B2 | 9/2006 | Berger |
| 7,115,597 B2 | 10/2006 | Bilodeau |

(Continued)

FOREIGN PATENT DOCUMENTS

| | | | |
|---|---|---|---|
| EP | 0 244 178 | 4/1987 | ............ A61K 47/00 |
| EP | 0 244 178 A | 11/1987 | |

(Continued)

OTHER PUBLICATIONS

Grisanti et al: "Intracameral Bevacizumab for Iris Rubeosis" American Journal of Ophthalmology, Ophthalmic Publ., Chicago, IL, US, vol. 142, No. 1, Jul. 1, 2006, pp. 158-160.
Iturralde Diana et al: "Intravitreal Bevacizumab (Avastin) Treatment of Macular Edema in Central Retinal Vein Occlusion: A Short-Term Study" Retina, Philadelphia, PA, US, vol. 26, No. 3, Jan. 1, 2006, pp. 279-284.
McCollum Gary W et al: "Herbimycin A inhibits angiogenic activity in endothelial cells and reduces neovascularization in a rat model of retinopathy of prematurity" Experimental Eye Research, vol. 78, No. 5, May 2004, pp. 987-995.
Mieler W et al: "Safety evaluation of second year treatment of age-related macular degeneration with pegaptanib sodium (Macugen): VEGF inhibition study in ocular neovascularization (VISION)" Investigative Ophthalmology & Visual Science, Ophthalmology, Hagerstown, MD, vol. 46, No. suppl, Jan. 1, 2005, p. 1380.

(Continued)

*Primary Examiner* — Jake Vu
(74) *Attorney, Agent, or Firm* — Laura L. Wine; Joel B. German

(57) ABSTRACT

Anti-angiogenesis compositions, and methods of using such compositions, useful for injection into the vitreous of human eyes are provided. Such compositions can include TKI component solutions or particles present in a therapeutically effective amount, a viscosity inducing component, and an aqueous carrier component. The compositions have viscosities at about 25° C. of at least about 10 cps or about 100 cps at a shear rate of 0.1/second. In a preferred embodiment, the viscosity at 25° C. is in the range of from about 80,000 cps to about 300,000 cps.

24 Claims, No Drawings

(56) References Cited

U.S. PATENT DOCUMENTS

| | | |
|---|---|---|
| 7,125,888 B2 | 10/2006 | Bilodeau |
| 7,157,577 B2 | 1/2007 | Tang |
| 7,223,724 B1 * | 5/2007 | Alderson et al. ............. 514/20.8 |
| 2001/0051620 A1 | 12/2001 | Berger |
| 2002/0091082 A1 | 7/2002 | Aiello |
| 2002/0122768 A1 | 9/2002 | Liu |
| 2002/0123513 A1 | 9/2002 | Krasner |
| 2002/0137755 A1 | 9/2002 | Bilodeau |
| 2002/0180294 A1 | 12/2002 | Kaneda |
| 2003/0050236 A1 | 3/2003 | Dawson |
| 2003/0055006 A1 | 3/2003 | Siemeister |
| 2003/0065180 A1 | 4/2003 | Tsou |
| 2003/0100567 A1 | 5/2003 | Bilodeau |
| 2003/0113897 A1 | 6/2003 | Hung |
| 2003/0124132 A1 | 7/2003 | Thorpe |
| 2003/0125235 A1 | 7/2003 | Foxwell |
| 2003/0125265 A1 | 7/2003 | Hung |
| 2003/0129193 A1 | 7/2003 | Thorpe |
| 2003/0130209 A1 | 7/2003 | Cheresh |
| 2003/0134884 A1 | 7/2003 | Hazama |
| 2003/0139374 A1 | 7/2003 | Thorpe |
| 2003/0175271 A1 | 9/2003 | Shitara |
| 2003/0181510 A1 | 9/2003 | Baker |
| 2003/0199478 A1 | 10/2003 | Andrews |
| 2003/0211075 A1 | 11/2003 | Thorpe |
| 2003/0219406 A1 | 11/2003 | Schroit |
| 2003/0224467 A1 | 12/2003 | Osborne |
| 2003/0224986 A1 | 12/2003 | Korsmeyer |
| 2003/0225152 A1 | 12/2003 | Andrews |
| 2003/0232741 A1 | 12/2003 | Neufeld |
| 2004/0005684 A1 | 1/2004 | Hung |
| 2004/0009965 A1 | 1/2004 | Collins |
| 2004/0023976 A1 | 2/2004 | Buchdunger |
| 2004/0023980 A1 | 2/2004 | Zhao |
| 2004/0023981 A1 | 2/2004 | Ren |
| 2004/0063720 A1 | 4/2004 | Bilodeau |
| 2004/0076622 A1 | 4/2004 | Studeny |
| 2004/0077601 A1 | 4/2004 | Adams |
| 2004/0086903 A1 | 5/2004 | Lareyre |
| 2004/0102360 A1 | 5/2004 | Barnett |
| 2004/0102509 A1 | 5/2004 | Andrews |
| 2004/0110762 A1 | 6/2004 | Berger |
| 2004/0121968 A1 | 6/2004 | Ljubimov |
| 2004/0127470 A1 | 7/2004 | Masferrer |
| 2004/0136950 A1 | 7/2004 | Ni |
| 2004/0136951 A1 | 7/2004 | Ni |
| 2004/0147449 A1 | 7/2004 | Siemeister |
| 2004/0147541 A1 | 7/2004 | Lane |
| 2004/0167079 A1 | 8/2004 | Tidmarsh |
| 2004/0167198 A1 | 8/2004 | Wrasidlo |
| 2004/0186126 A1 | 9/2004 | Collins |
| 2004/0192725 A1 | 9/2004 | Kim |
| 2004/0192926 A1 | 9/2004 | Hartman |
| 2004/0198802 A1 | 10/2004 | Andrews |
| 2004/0214836 A1 | 10/2004 | Cheresh |
| 2004/0220196 A1 | 11/2004 | Hannah |
| 2004/0220216 A1 | 11/2004 | Arrington |
| 2004/0228872 A1 | 11/2004 | Bonner |
| 2004/0235826 A1 | 11/2004 | Peckham |
| 2004/0242637 A1 | 12/2004 | Harman |
| 2005/0070508 A1 | 3/2005 | Lou |
| 2005/0070546 A1 | 3/2005 | Arrington |
| 2005/0084490 A1 | 4/2005 | Adams |
| 2005/0090498 A1 | 4/2005 | Samizu |
| 2005/0090509 A1 | 4/2005 | Lou |
| 2005/0090732 A1 | 4/2005 | Ivkov |
| 2005/0096257 A1 | 5/2005 | Shima |
| 2005/0107399 A1 | 5/2005 | Boman |
| 2005/0112090 A9 | 5/2005 | Ni |
| 2005/0113297 A1 | 5/2005 | Francois |
| 2005/0118154 A1 | 6/2005 | Hung |
| 2005/0129616 A1 | 6/2005 | Salcedo |
| 2005/0129699 A1 | 6/2005 | Salcedo |
| 2005/0137395 A1 | 6/2005 | Hong |
| 2005/0143817 A1 | 6/2005 | Hunter |
| 2005/0149080 A1 | 7/2005 | Hunter |
| 2005/0149158 A1 | 7/2005 | Hunter |
| 2005/0152946 A1 | 7/2005 | Hunter |
| 2005/0153990 A1 | 7/2005 | Watkins |
| 2005/0154374 A1 | 7/2005 | Hunter |
| 2005/0158356 A1 | 7/2005 | Hunter |
| 2005/0165488 A1 | 7/2005 | Hunter |
| 2005/0169960 A1 | 8/2005 | Hunter |
| 2005/0169961 A1 | 8/2005 | Hunter |
| 2005/0175663 A1 | 8/2005 | Hunter |
| 2005/0175665 A1 | 8/2005 | Hunter |
| 2005/0175703 A1 | 8/2005 | Hunter |
| 2005/0176753 A1 | 8/2005 | Bilodeau |
| 2005/0176776 A1 | 8/2005 | Coleman |
| 2005/0177225 A1 | 8/2005 | Hunter |
| 2005/0178395 A1 | 8/2005 | Hunter |
| 2005/0178396 A1 | 8/2005 | Hunter |
| 2005/0181005 A1 | 8/2005 | Hunter |
| 2005/0181008 A1 | 8/2005 | Hunter |
| 2005/0181009 A1 | 8/2005 | Hunter |
| 2005/0181010 A1 | 8/2005 | Hunter |
| 2005/0181011 A1 | 8/2005 | Hunter |
| 2005/0181977 A1 | 8/2005 | Hunter |
| 2005/0182463 A1 | 8/2005 | Hunter |
| 2005/0183728 A1 | 8/2005 | Hunter |
| 2005/0183731 A1 | 8/2005 | Hunter |
| 2005/0186239 A1 | 8/2005 | Hunter |
| 2005/0186244 A1 | 8/2005 | Hunter |
| 2005/0186245 A1 | 8/2005 | Hunter |
| 2005/0186637 A1 | 8/2005 | Yu |
| 2005/0187140 A1 | 8/2005 | Hunter |
| 2005/0191331 A1 | 9/2005 | Hunter |
| 2005/0192429 A1 | 9/2005 | Rosen |
| 2005/0196421 A1 | 9/2005 | Hunter |
| 2005/0197401 A1 | 9/2005 | Sebti |
| 2005/0202075 A1 | 9/2005 | Pardridge |
| 2005/0208095 A1 | 9/2005 | Hunter |
| 2005/0214205 A1 | 9/2005 | Salcedo |
| 2005/0214206 A1 | 9/2005 | Salcedo |
| 2005/0214207 A1 | 9/2005 | Salcedo |
| 2005/0214208 A1 | 9/2005 | Salcedo |
| 2005/0214209 A1 | 9/2005 | Salcedo |
| 2005/0214210 A1 | 9/2005 | Salcedo |
| 2005/0215465 A1 | 9/2005 | Groen |
| 2005/0220768 A1 | 10/2005 | McVey |
| 2005/0220781 A1 | 10/2005 | Yan |
| 2005/0222163 A1 | 10/2005 | Eck |
| 2005/0227929 A1 | 10/2005 | Masferrer |
| 2005/0227988 A1 | 10/2005 | Trotter |
| 2005/0228031 A1 | 10/2005 | Bilodeau |
| 2005/0232921 A1 | 10/2005 | Rosen |
| 2005/0233958 A1 | 10/2005 | Ni |
| 2005/0239815 A1 | 10/2005 | Kim |
| 2005/0244408 A1 | 11/2005 | Cohen |
| 2005/0244467 A1 | 11/2005 | Nivaggioli |
| 2005/0244469 A1 | 11/2005 | Whitcup |
| 2005/0244475 A1 | 11/2005 | Edelman |
| 2005/0244477 A1 | 11/2005 | Hughes |
| 2005/0244857 A1 | 11/2005 | Ni |
| 2005/0245462 A1 | 11/2005 | Tidmarsh |
| 2005/0255532 A1 | 11/2005 | Ruben |
| 2005/0261253 A1 | 11/2005 | Cannizzaro |
| 2005/0261496 A1 | 11/2005 | Dinsmore |
| 2005/0267087 A1 | 12/2005 | Poulaki |
| 2005/0272759 A1 | 12/2005 | Moon |
| 2005/0281812 A1 | 12/2005 | Cohen |
| 2005/0281883 A1 | 12/2005 | Daniloff |
| 2005/0282814 A1 | 12/2005 | Wrasidlo |
| 2005/0282852 A1 | 12/2005 | Yamazaki |
| 2006/0003322 A1 | 1/2006 | Bentwich |
| 2006/0003966 A1 | 1/2006 | Arbiser |
| 2006/0010505 A1 | 1/2006 | Baranski |
| 2006/0013823 A1 | 1/2006 | Kim |
| 2006/0040335 A1 | 2/2006 | Butt |
| 2006/0057138 A1 | 3/2006 | Wood |
| 2006/0062786 A1 | 3/2006 | Salcedo |
| 2006/0063736 A1 | 3/2006 | Bertozzi |
| 2006/0073182 A1 | 4/2006 | Wong |
| 2006/0079526 A1 | 4/2006 | Wrasidlo |

(56) References Cited

U.S. PATENT DOCUMENTS

| | | |
|---|---|---|
| 2006/0079548 A1 | 4/2006 | Collins |
| 2006/0100227 A1 | 5/2006 | Baenteli |
| 2006/0111423 A1 | 5/2006 | Zeligs |
| 2006/0128783 A1 | 6/2006 | Dinsmore |
| 2006/0135423 A1 | 6/2006 | Ambati |
| 2006/0135443 A1 | 6/2006 | Khodadoust |
| 2006/0147492 A1 | 7/2006 | Hunter |
| 2006/0147959 A1 | 7/2006 | Bell |
| 2006/0154285 A1 | 7/2006 | Robishaw |
| 2006/0156421 A1 | 7/2006 | Cagan |
| 2006/0167036 A1 | 7/2006 | Kim |
| 2006/0167083 A1 | 7/2006 | Kelly |
| 2006/0182783 A1 | 8/2006 | Hughes et al. |
| 2006/0183684 A1 | 8/2006 | Cedarbaum |
| 2006/0189577 A1 | 8/2006 | Kim |
| 2006/0189608 A1 | 8/2006 | Bingaman |
| 2006/0193772 A1 | 8/2006 | Ochiai |
| 2006/0205765 A1 | 9/2006 | Bilodeau |
| 2006/0223096 A1 | 10/2006 | Umana |
| 2006/0230359 A1 | 10/2006 | Fischer |
| 2006/0233141 A1 | 10/2006 | Iyer |
| 2006/0247217 A1 | 11/2006 | Berger |
| 2006/0247237 A1 | 11/2006 | Freyne |
| 2006/0247250 A1 | 11/2006 | Cao |
| 2006/0258686 A1 | 11/2006 | Cheresh |
| 2006/0258696 A1 | 11/2006 | Moss |
| 2006/0263434 A1 | 11/2006 | Desai |
| 2006/0264495 A1 | 11/2006 | Palladino |
| 2006/0269555 A1 | 11/2006 | Salcedo |
| 2006/0270673 A1 | 11/2006 | Duggan |
| 2006/0270837 A1 | 11/2006 | Salcedo |
| 2006/0276294 A1 | 12/2006 | Coffey |
| 2006/0276514 A1 | 12/2006 | Kim |
| 2006/0276527 A1 | 12/2006 | Tidmarsh |
| 2006/0280747 A1 | 12/2006 | Fuh |
| 2006/0293358 A1 | 12/2006 | Dinsmore |
| 2007/0004676 A1 | 1/2007 | Palladino et al. |
| 2007/0015752 A1 | 1/2007 | Hangauer |
| 2008/0268051 A1 | 10/2008 | Hughes et al. |

FOREIGN PATENT DOCUMENTS

| | | |
|---|---|---|
| EP | 2146727 | 4/2012 |
| WO | WO01/49226 A | 7/2001 |
| WO | WO03/084951 A | 10/2003 |
| WO | WO 2005/046641 | 5/2005 |
| WO | WO2005/072701 | 8/2005 |
| WO | WO2005/107708 A | 11/2005 |
| WO | WO2006/086750 | 8/2006 |
| WO | WO2007/037849 | 4/2007 |
| WO | WO2007/047607 | 4/2007 |
| WO | WO2008/061236 A | 5/2008 |
| WO | WO2008/134644 | 11/2008 |

OTHER PUBLICATIONS

Nguyen et al: "Vascular Endothelial Growth Factor is a Critical Stimulus for Diabetic Macular Edema" American Journal of Ophthalmology, Ophthalmic Publ., Chicago, IL, US, vol. 142, No. 6, Dec. 6, 2006, pp. 961-969.

Spaide Richard F et al: "Intravitreal bevacizumab treatment of choroidal neovascularization secondary to age-related macular degeneration" Retina, Philadelphia, PA, US, vol. 26, No. 4, Apr. 1, 2006, pp. 383-390.

U.S. Appl. No. 10/256,879, filed Sep. 27, 2002, Andrews.

U.S. Appl. No. 10/259,703, filed Sep. 27, 2002, Andrews.

Antcliff R., et al Marshall J., *The pathogenesis of edema in diabetic maculopathy*, Semin Ophthalmol 1999; 14:223-232.

Busse et al., "Tyrosine kinase inhibitors: rationale, mechanisms of action, and implications for drug resistance", Semin Oncol 28(suppl 16) 47-55 (2001).

Einmahl S. et al, *Evaluation of a novel biomaterial in the suprachoroidal space of the rabbit eye*, Invest Ophthal & Vis Sci 43(5); 1533-1539 (2002).

Einmahl S. et al, *Therapeutic applications of viscous and injectable poly(ortho esters)*, Adv Drug Del Rev 53 (2001) 45-73.

Fabbro et al., "Protein tyrosine kinase inhibitors: new treatment modalities?", Current Opinion in Pharmacology, 2:374-381 (2002).

Goel et al., "Tyrosine Kinase Inhibitors: A Clinical Perspective", Current Oncology Reports, 4:9-19 (2002).

Haluska et al., "Receptor tyrosine kinase inhibitors", Current Opinion in Investigational Drugs, 2(2):280-286 (2001).

Hubbard et al., "Protein tyrosine kinase structure and function", Annu. Rev. Biochem., 69:373-398 (2000).

Pe'er J. et al., *Vascular endothelial growth factor upregulation in human central retinal vein occlusion*, Ophthalmology 1998; 105:412-416.

U.S. Appl. No. 11/742,350, filed Apr. 30, 2007.

* cited by examiner

METHODS AND COMPOSITIONS FOR INTRAOCULAR ADMINISTRATION TO TREAT OCULAR CONDITIONS

BACKGROUND

The present invention relates to ophthalmically useful compositions comprising a viscosity inducing component and an active pharmaceutical agent. In preferred embodiments, the pharmaceutically active agent can comprise a tyrosine kinase inhibitor ("TKI") or other anti-angiogenesis agent. The invention also relates to methods for treating and/or preventing ocular conditions, such as anterior ocular conditions and posterior ocular conditions. In a preferred embodiment the present invention relates to extended release and sustained release therapeutic compositions comprising ophthalmically acceptable gels and liquid formulations comprising a viscosity inducing component and a tyrosine kinase inhibitor.

A pharmaceutical composition (synonymously a "composition") is a formulation which contains at least one active ingredient (for example a tyrosine or serine kinase inhibitor capable of inhibiting angiogenesis (collectively, "TKIs" unless identified specifically or separately), or another anti-angiogenesis agent) together with a viscosity enhancing component. In certain embodiments the composition may also contain one or more excipients, such as a tonicity adjusting agent, an anti-oxidant, buffers, carriers, stabilizers, preservatives and/or bulking agents, and is suitable for administration to a patient to achieve a desired effect or result. The pharmaceutical compositions disclosed herein can have diagnostic, therapeutic, cosmetic and/or research utility in various species, such as for example in human patients or subjects.

A variety of ocular conditions involve a disease, ailment or condition which affects or involves the eye or one of the parts or regions of the eye and is characterized to a major or minor degree by angiogenesis (the formation of new blood vessels).

Broadly speaking, the eye includes the eyeball and the tissues and fluids which constitute the eyeball, the periocular muscles (such as the oblique and rectus muscles) and the portion of the optic nerve which is within or adjacent to the eyeball. An anterior ocular condition is a disease, ailment or condition which affects or which involves an anterior (i.e. front of the eye) ocular region or site, such as a periocular muscle, an eyelid or an eyeball tissue or fluid which is located anterior to the posterior wall of the lens capsule or ciliary muscles. Thus, an anterior ocular condition primarily affects or involves, the conjunctiva, the cornea, the conjunctiva, the anterior chamber, the iris, the posterior chamber (anterior to the retina but in posterior to the posterior wall of the lens capsule), the lens or the lens capsule and blood vessels and nerve which vascularize or innervate an anterior ocular region or site.

A condition of the posterior segment (posterior ocular condition) of the eye is a disease, ailment or condition which significantly affects or involves a tissue or cell type in a posterior ocular region or site (that is, in a position posterior to a plane through the posterior wall of the lens capsule), such as the accordingly located parts of the choroid or sclera, vitreous, vitreous chamber, retina, optic nerve (i.e. the optic disc), and blood vessels and nerves which vascularize or innervate a posterior ocular (or posterior segment) region or site.

Thus, a posterior ocular condition can include a disease, ailment or condition, such as for example, macular degeneration (such as non-exudative age-related macular degeneration and exudative age-related macular degeneration); choroidal neovascularization; acute macular neuroretinopathy; macular edema (such as cystoid macular edema and diabetic macular edema); Behcet's disease, retinal disorders, diabetic retinopathy (including proliferative diabetic retinopathy); retinal arterial occlusive disease; central retinal vein occlusion; uveitis (including intermediate and anterior uveitis); retinal detachment; ocular trauma which affects a posterior ocular site or location; a posterior ocular condition caused by or influenced by an ocular laser treatment; posterior ocular conditions caused by or influenced by a photodynamic therapy; photocoagulation; radiation retinopathy; epiretinal membrane disorders; branch retinal vein occlusion; anterior ischemic optic neuropathy; non-retinopathy diabetic retinal dysfunction, retinitis pigmentosa and glaucoma. Glaucoma can be considered a posterior ocular condition because a therapeutic goal can be to prevent the loss of or reduce the occurrence of loss of vision due to damage to or loss of retinal cells or optic nerve cells (i.e. neuroprotection). The infiltrative growth of new blood vessels can disrupt or destroy nervous tissue; thus the inhibition of angiogenesis can also be considered to provide protection to affected neurons.

Macular edema is a major cause of visual loss in patients, and can accompany a number of pathological conditions, including, without limitation, diabetes, central retinal vein occlusion (CRVO) and branch retinal vein occlusion (BRVO). Although laser photocoagulation can reduce further vision loss in patients with diabetic macular edema (DME), vision that has already been decreased by macular edema through neural cell death usually does not improve appreciably by use of laser photocoagulation. Currently, there is no FDA (U.S. Food and Drug Administration) approved treatment for macular edema associated with CRVO. For macular edema associated with BRVO, grid laser photocoagulation may be an effective treatment for some patients.

Diabetic macular edema is characterized abnormal leakage of macromolecules, such as lipoproteins, from retinal capillaries into the extravascular space followed by an oncotic influx of water into the extravascular space. The leakage may be caused by or exacerbated by the growth of new blood vessels (angiogenesis). Abnormalities in the retinal pigment epithelium (RPE) may also cause or contribute to diabetic macular edema. These abnormalities can allow increased fluid from the choriocapillaries to enter the retina or they may decrease the normal efflux of fluid from the retina to the choriocapillaries. The breakdown of the blood-retina barrier at the level of the retinal capillaries and the retinal pigment epithelium may also be accompanied or caused by changes to tight junction proteins such as occluding. Antcliff R., et al Marshall J., *The pathogenesis of edema in diabetic maculopathy*, Semin Ophthalmol 1999; 14:223-232.

Macular edema from venous occlusive disease can result from thrombus formation at the lamina cribrosa or at an arteriovenous crossing. These changes can result in an increase in retinal capillary permeability and accompanying retinal edema. The increase in retinal capillary permeability and subsequent retinal edema can ensue from of a breakdown of the blood retina barrier mediated in part by vascular endothelial growth factor (VEGF), a 45 kD glycoprotein. It is known that VEGF can increase vascular permeability; possibly by increasing phosphorylation of tight junction proteins such as occludin and zonula occluden. Similarly, in human non-ocular disease states such as ascites, VEGF has been characterized as a potent vascular permeability factor (VPF).

Biochemically, VEGF is known to be a major contributor to the increase in the number of capillaries in tissue undergoing angiogenesis. Bovine capillary endothelial cells will proliferate and show signs of tube structures in vitro upon stimulation by VEGF. Upregulation of VEGF is a major component of the physiological response to exercise and its role in angiogenesis is suspected to be a possible treatment in vascular injuries.

VEGF causes an intracellular signaling cascade in endothelial cells. VEGF binding to VEGF receptor-2 (VEGFR-2) initiates a tyrosine kinase signaling cascade that stimulates the production of factors that variously stimulate vessel permeability (epithelial nitric oxide synthase; (eNOS), proliferation/survival (bFGE; basic fibroblast growth factor), migration (intercellular adhesion molecules (ICAMs); vascular cell adhesion molecules (VCAMs); matrix metalloproteases (MMPs)) and finally differentiation into mature blood vessels. As part of the angiogenic signaling cascade, NO (nitric oxide) is widely considered to be a major contributor to the angiogenic response because inhibition of NO significantly reduces the effects of angiogenic growth factors.

The normal human retina contains little or no VEGF; however, hypoxia causes upregulation of VEGF production. Disease states characterized by hypoxia-induced VEGF upregulation include, without limitation, CRVO and BRVO. This hypoxia induced upregulation of VEGF can be inhibited pharmacologically. Pe'er J. et al., *Vascular endothelial growth factor upregulation in human central retinal vein occlusion*, OPHTHALMOLOGY 1998; 105 412-416. It has been demonstrated that anti-VEGF antibodies can inhibit VEGF driven capillary endothelial cell proliferation. Thus, attenuation of the effects of VEGF introduces a rationale for treatment of macular edema from venous occlusive disease.

Additionally, overexpression of VEGF causes increased permeability in blood vessels in addition to stimulating angiogenesis. In "wet" or exudative macular degeneration, VEGF causes proliferation of capillaries into the retina. Since the increase in angiogenesis also causes edema, blood and other retinal fluids leak into the retina causing loss of vision. A novel treatment for macular degeneration is to use a VEGF inhibiting aptamer, or other VEGF-inhibiting compound, such as a TKI, to stop the main signaling cascade for angiogenesis, thereby preventing these symptoms.

European patent application 244 178 A2 (Keller) discloses intravitreal injection of an aqueous solution of dexamethasone, a steroid, and a hyaluronic acid (HA). Einmahl S. et al, *Evaluation of a novel biomaterial in the suprachoroidal space of the rabbit eye*, INVEST OPHTHAL & VIS SCI 43(5); 1533-1539 (2002) discusses injection of a poly(ortho ester) into the suprachoroidal space, and Einmahl S. et al, *Therapeutic applications of viscous and injectable poly(ortho esters)*, ADV DRUG DEL REV 53 (2001) 45-73, discloses that a poly ortho ester polymer containing fluorouracil markedly degrades five days after intravitreal administration. European Patent Publication EP 0 244 178 describes HA compositions for intraocular injection containing antibiotics or anti-inflammatory agents. Della Valle et al., U.S. Pat. No. 5,166,331 discusses purification of different fractions of HA for use as a substitute for intraocular fluids and as a topical ophthalmic drug carrier.

SUMMARY

In one embodiment the present invention provides formulations comprising one or more TKI (such as a tyrosine kinase inhibitor or a serine kinase inhibitor) in a biocompatible viscous carrier suitable for intraocular (including, without limitation, intravitreal, subconjuntival, and subretinal) injection or placement for treating ocular angiogenesis, particularly angiogenesis in the retina, including the macula; the choroid, the sclera and other features of the posterior segment of the eye, as may be manifested in the development of, e.g., macular edema, dry and wet macular degeneration, particularly exudative macular degeneration, diabetic retinopathy and other disorders and diseases involving angiogenesis. In a preferred embodiment, the carrier comprises a hyaluronic acid component, preferably at least one polyhyaluronic acid component of defined average molecular weight.

DEFINITIONS

As used herein, the words or terms set forth below have the following definitions.

"About" means that the item, parameter or term so qualified encompasses a range of plus or minus ten percent above and below the value of the stated item, parameter or term.

"Administration", or "to administer" means the step of giving (i.e. providing) a pharmaceutical composition to a subject. The pharmaceutical compositions disclosed herein can be "locally administered", that is administered at or in the vicinity of the site at which a therapeutic result or outcome is desired. For example to treat an ocular condition (such as for example a macular edema, or macular degeneration) intravitreal injection or implantation of a therapeutic composition such as active agent-containing viscous composition can be carried out, and is an example of local administration.

"Entirely free (i.e. "consisting of" terminology) means that within the detection range of the instrument or process being used or referenced, the substance cannot be detected or its presence cannot be conclusively confirmed.

"Essentially free" means that only trace amounts of other substances, or a reference substance (such trace amounts not having a substantial effect in the application), can be detected.

"Pharmaceutical composition" means a formulation in which an active ingredient (the active agent) can be an inhibitor of angiogenesis, such as a TKI. The word "formulation" means that there is at least one additional ingredient in the pharmaceutical composition besides the active ingredient. A pharmaceutical composition is therefore a formulation which is suitable for diagnostic or therapeutic administration (e.g., by intraocular injection or by insertion of a depot or implant) to a subject, such as a human patient.

"Substantially free" means present at a level of less than one percent by weight of the pharmaceutical composition.

Viscosity values in the specification or the claims mean the viscosity at 25° C. (unless another temperature is stated) at a shear rate of about 0.1/second of between about 100 cps to about 300,000 cps.

Each range of values (amounts, viscosities, temperatures and the like) specifically includes, and shall be regarded as containing a complete written description of) all values and sub-ranges between the minimum and maximum.

The present compositions are highly suitable for intravitreal administration into the posterior segments of eyes without requiring any washing step, while providing for reduced ocular, for example, retinal, damage when used in an eye. Overall, the present compositions are easily and effectively injectable into the posterior segment of an eye of a human or animal. An advantage of the formulations of the present invention is that the TKI component is present in a viscous carrier comprising a viscosity inducing component which is biologically compatible, that is, has no substantial deleterious or cytotoxic effects on the cells of the eye.

In one broad aspect of the present invention, compositions useful for injection into a posterior segment of an eye of a human or animal are provided. Such compositions comprise a TKI component, a viscosity inducing component, and an aqueous carrier component. The TKI component is present in a therapeutically effective amount. The TKI component is preferably present in the compositions in solution, but may initially be present in somewhat or partly insoluble form, such as in a plurality of particles.

The present compositions may include a TKI component in an amount of up to about 25% (w/v) or more of the composition. In one very useful embodiment, the TKI component is present in an amount up to at least about 80 mg/ml of composition. Preferably, the TKI component is present in an amount in a range of about 1% to about 10% or about 20% (w/v) of the composition, or about 0.2 mg per 100 μl or about 0.4 mg per 100 μl, or about 0.5 mg per 100 μl, or about 1.0 mg per 100 μl or about 2.0 mg per 100 μl, or about 4.0 mg per 100 μl, or about 5.0 mg per 100 μl, or about 6.0 mg per 100 μl, or about 7.0 mg per 100 μl, or about 8.0 mg per 100 μl, or about 10 mg per 100 μl, or about 20 mg per 100 μl, or about 40 mg per 100 μl, or about 60 mg per 100 μl, or about 80 mg per 100 μl.

In particular, the TKIs of the present invention are inhibitors of angiogenesis, particularly ocular angiogenesis, such as choroidal neovascularization (CNV) accompanying a condition such as macular degeneration, in particular, though not exclusively, exudative macular degeneration, diabetic retinopathy, retinal ischemia and macular edema.

Vascular epithelial growth factor (VEGF-A) is a generic name for a family of signaling proteins involved in angiogenesis (the growth of blood vessels from pre-existing vasculature). VEGF also enhances microvascular permeability. This family of proteins comprise splice variants resulting from alternative splicing of a single gene. There are other VEGF-like proteins, including VEGF-B, VEGF-C and VEGF-D and PlGF.

All members of the VEGF family stimulate cellular responses by binding to tyrosine kinase receptors (the VEGFRs) on the cell surface. Ligand binding induces dimerization which activates the tyrosine kinase activity of the receptor. This leads to receptor autophosphorylation and the initiation of intracellular signal transduction cascades causing the receptors to dimerize and become activated through transphosphorylation involving the tyrosine kinase. The VEGF receptors have an extracellular portion consisting of 7 immunoglobulin-like domains, a single transmembrane spanning region and an intracellular portion containing a split tyrosine kinase domain.

Various approaches have been made to inhibit either VEGF itself or the VEGFR present in the eye in order to prevent angiogenesis. Thus, monoclonal antibodies such as ranibizumab and bevacizumab; nucleic acids (aptamers such as MACUGEN®, (pegaptanib) a PEGylated RNA aptamer, and siRNAs directed to VEGF RNA), and both protein and small molecule tyrosine kinase inhibitors have been investigated for the treatment of angiogenesis associated with conditions of the posterior segment.

As stated above, hypoxia is known to upregulate VEGF expression, and VEGF expression was shown to be correlated with iris neovascularization in primate models of ischemic retinal vein occlusion and retinal neovascularization. Injection of VEGF in normal primate eyes produces iris neovascularization, neovascular glaucoma, and retinal microaniopathy. Inhibition of VEGF through the use of chimeric proteins acting as soluble VEGF receptors suppresses neovascularization in these models.

Human clinical studies have also confirmed the association of VEGF expression with pathologic ocular neovascularization. Measurements of vitreous VEGF levels demonstrated significantly higher VEGF concentrations in patients with active proliferative diabetic retinopathy compared with patients with other retinal disorders not characterized by abnormal blood vessel growth. Another study that analyzed both aqueous and vitreous levels of VEGF in a variety of conditions characterized by ocular neovascularization correlated elevated VEGF concentrations in ocular fluids of patients with active neovascularization.

Inhibition of tyrosine kinase activity (and particularly VEGFR-associated tyrosine kinase activated signal transduction) in the posterior segment of the eye may be accomplished using any of a number of TKIs that have activity against activation of the tyrosine kinase activity of the VEGFR. These may include TKIs listed or disclosed in one or more of the following United States patents:

U.S. Pat. No. 7,157,577; U.S. Pat. No. 7,125,888; U.S. Pat. No. 7,115,597; U.S. Pat. No. 7,115,597; U.S. Pat. No. 7,105,531; U.S. Pat. No. 7,101,884; U.S. Pat. No. 7,098,236; U.S. Pat. No. 7,091,181; U.S. Pat. No. 6,071,332; U.S. Pat. No. 7,053,113; U.S. Pat. No. 7,045,528; U.S. Pat. No. 7,037,498; U.S. Pat. No. 7,015,220; U.S. Pat. No. 7,008,943; U.S. Pat. No. 7,005,444; U.S. Pat. No. 6,995,162; U.S. Pat. No. 6,979,675; U.S. Pat. No. 6,933,299; U.S. Pat. No. 6,927,293; U.S. Pat. No. 6,906,093; U.S. Pat. No. 6,878,714; U.S. Pat. No. 6,875,767; U.S. Pat. No. 6,872,724; U.S. Pat. No. 6,869,962; U.S. Pat. No. 6,855,730; U.S. Pat. No. 6,777,439; U.S. Pat. No. 6,767,025; U.S. Pat. No. 6,716,870; U.S. Pat. No. 6,713,474; U.S. Pat. No. 6,710,067; U.S. Pat. No. 6,709,709; U.S. Pat. No. 6,699,863; U.S. Pat. No. 6,689,806; U.S. Pat. No. 6,685,938; U.S. Pat. No. 6,680,048; U.S. Pat. No. 6,559,173; U.S. Pat. No. 6,531,502; U.S. Pat. No. 6,514,981; U.S. Pat. No. 6,482,848; U.S. Pat. No. 6,465,507, U.S. Pat. No. 6,451,838; U.S. Pat. No. 6,399,655; U.S. Pat. No. 6,395,734; U.S. Pat. No. 6,344,455; U.S. Pat. No. 6,331,555; U.S. Pat. No. 6,028,099; U.S. Pat. No. 5,990,141; U.S. Pat. No. 5,980,929; U.S. Pat. No. 5,958,959; U.S. Pat. No. 5,919,813; U.S. Pat. No. 5,914,343; U.S. Pat. No. 5,795,910; U.S. Pat. No. 5,776,902; U.S. Pat. No. 5,760,066; U.S. Pat. No. 5,728,726; U.S. Pat. No. 5,721,277; U.S. Pat. No. 5,700,822; U.S. Pat. No. 5,674,892; U.S. Pat. No. 5,580,979;

and in one or more of the following U.S. Patent Publications: 20070015752; 20070004676; 20060293358; 20060280747; 20060276527; 20060276514; 20060276294; 20060270837; 20060270673; 20060269555; 20060264495; 20060263434; 20060258696; 20060258686; 20060247250; 20060247250; 20060247237; 20060247217; 20060230359; 20060233141; 20060223096; 20060205765; 20060193772; 20060189608; 20060189577; 20060183684; 20060167083; 20060167036; 20060156421; 20060154285; 20060147959; 20060147492; 20060135443; 20060135423; 20060128783; 20060111423; 20060100227; 20060079548; 20060079526; 20060073182; 20060063736; 20060062786; 20060057138; 20060040335; 20060013823; 20060010505; 20060003966; 20060003322; 20050282852; 20050282814; 20050281883; 20050281812; 20050272759; 20050267087; 20050261496; 20050261253; 20050255532; 20050245462; 20050244857; 20050244477; 20050244475; 20050244469; 20050244467; 20050244408; 20050239815; 20050233958; 20050232921; 20050228031; 20050227988; 20050227929; 20050222163; 20050220781; 20050220768; 20050215465; 20050214210; 20050214209; 20050214208; 20050214207; 20050214206; 20050214205; 20050208095; 20050202075; 20050197401; 20050196421; 20050192429; 20050191331; 20050187140; 20050186637; 20050186245; 20050186244; 20050186239; 20050183731; 20050183728; 20050182463; 20050181977; 20050181011; 20050181010; 20050181009; 20050181008; 20050181005; 20050178396; 20050178395; 20050177225; 20050176776; 20050176753; 20050175703; 20050175665; 20050175663; 20050169961; 20050169960; 20050165488; 20050158356;

20050154374; 20050153990; 20050152946; 20050149158; 20050149080; 20050143817; 20050137395; 20050129699; 20050129616; 20050118154; 20050113297; 20050112090; 20050107399; 20050096257; 20050090732; 20050090509; 20050090498; 20050084490; 20050070546; 20050070508; 20040242637; 20040235826; 20040228872; 20040220216; 20040220196; 20040214836; 20040198802; 20040192926; 20040192725; 20040186126; 20040167198; 20040167079; 20040147541; 20040147449; 20040136951; 20040136950; 20040127470; 20040121968; 20040110762; 20040102509; 20040102360; 10040086903; 20040077601; 20040076622; 20040063720; 20040023981; 20040023980; 20040023976; 20040009965; 20040005684; 20030232741; 20030224986; 20030224467; 20030219406; 20030211075; 20030181510; 20020180294; 20030175271; 20030139374; 20030134884; 20030130209; 20030129193; 20030125265; 20030125235; 200301.24132; 20030113897; 20030100567; 20030065180; 20030055006; 20030050236; 20020137755; 20020123513; 20020122768; 20020091082; 20010051620.

Each and every of these patents and patent applications is hereby incorporated by reference herein in its entirety as part of the present specification.

In one embodiment, the present compositions and methods may, without exception, comprise TKI component which includes a macromolecule, such as a protein, peptide, (including modified protein or peptides and/or peptidomimetics) or a nucleic acid or modified nucleic acid, such as one containing modified nucleoside or ribonucleoside residues, or a peptide nucleic acid or other nucleic mimetic. Additionally, or alternative, the TKI component may comprise an organic molecule other than a macromolecule; these organic, non-macromolecular TKI components shall be referred to herein as "small molecules".

The viscosity inducing component of the present compositions is present in an amount effective to increase the viscosity of the composition, which is usually an aqueous composition. The viscosity inducing component is very preferably substantially or perfectly clear. Any suitable, ophthalmically acceptable, viscosity inducing component may be employed in accordance with the present invention. Viscosity inducing components have been proposed, known, and/or used in ophthalmic compositions for treatment of the eye. Advantageously, the viscosity inducing component is present in an amount in a range of about 0.5% to about 20% (w/v) of the composition. In one particularly useful embodiment, the viscosity inducing component is a hyaluronic acid polymer component, such as sodium hyaluronate.

In a particularly preferred embodiment, the viscosity inducing component is substantially clear in solution, and present in an amount such that the refractive index of the resulting TKI-containing composition is substantially similar to that of the vitreous humor, in order to prevent drastic and deleterious changes in vision after administration (such as intraocular delivery) of the composition to a patient. This is particularly desirable if the composition is injected into the posterior segment of the eye. In such cases, preferably the refractive index of the resulting TKI-containing composition is substantially identical to that of the vitreous humor. However, these parameters may be less critical when the composition is administered by other means, e.g., by way of subconjuctival or subretinal delivery.

In one embodiment, the present composition can have a viscosity of at least about 10 cps or at least about 100 cps, preferably at least about 1,000 cps, more preferably at least about 10,000 cps and still more preferably at least about 70,000 cps, for example, up to about 250,000 cps, or about 300,000 cps, at a shear rate of 0.1/second at about 25° C.

Preferably, the present compositions are structured or formulated to be effectively, for example, manually, injected into a posterior segment of an eye of a human or animal, preferably through a 27 gauge needle, more preferably through a 29 or 30 gauge needle.

Without wishing to limit the invention to any particular theory of operation, it is believed that the use of relatively high viscosity compositions, as described herein, provides for effective, and preferably substantially long-lasting delivery of the while, at the same time, being injectable into the posterior segment of an eye through conventionally, or even smaller than conventionally, used needles. In embodiments in which the TKI component is delivered in part as marginally or slowly soluble particles, the viscosity-inducing component is also effective to aid in keeping the particles in suspension, rather than being largely or mostly simply deposited on the bottom surface of the posterior segment of the eye.

In one embodiment of the invention, the TKI component is present in a plurality of particles which are substantially uniformly suspended in the composition and remain substantially uniformly suspended in the composition for at least about 1 week, preferably at least about 2 weeks or at least about 1 month, and still more preferably at least about 6 months or at least about 1 year or at least about 2 years, without requiring resuspension processing, that is, without requiring being shaken or otherwise agitated to maintain the TKI component particles substantially uniformly suspended in the composition.

Compositions having such substantially uniform suspension of TKI component particles, so as to be able to provide a consistent and accurate dose upon administration to an eye, provide substantial advantages relative to the prior art. In particular, the present compositions may be manufactured, shipped and stored for substantial periods of time without the TKI component particles precipitating from the remainder of the composition. Having the TKI component particles maintained substantially uniformly suspended in the composition allows the composition to provide long term dosing consistency and accuracy per unit dose amount administered, without any need to resuspend the TKI panicles.

The aqueous carrier component is advantageously ophthalmically acceptable and may include one or more conventional expedients useful in ophthalmic compositions. For example, the carrier component may include an effective amount of at least one of a preservative component, a tonicity component and/or a buffer component. However, in one advantageous embodiment, the present compositions include no added preservative component. This feature reduces or minimizes or even substantially eliminates adverse reactions, such as cytotoxicity, in the eye which may be caused by or linked to the presence of a preservative component, particularly conventional preservatives such as benzalkonium chloride (known as BAC or BAK), and quaternary ammonium preservatives.

Methods of treating posterior segments of the eyes of humans or animals are also disclosed and are included within the scope of the present invention. In general, such methods comprise administering, e.g. injecting a TKI component-containing composition, for example, a composition in accordance with the present invention, to a posterior segment of an eye of a human or animal, such as into the vitreous humor of said eye. Such administering step is effective in providing a desired therapeutic effect to the tissues of the posterior segment. The administering step preferably comprises at least one of intravitreal injecting or placement, subconjunctival injecting or placement, sub-tenon injecting or placement, retrobulbar injecting or placement, suprachoroidal injecting or placement and the like.

The present invention encompasses a pharmaceutical composition for treating a posterior ocular condition, which term is defined below. The composition can comprise a TKI component; a viscosity inducing component in an amount effective to increase the viscosity of the composition, and; an aqueous carrier component. The composition can have a viscosity of at least about 10 cps at a shear rate of about 0.1/second and is injectable into the vitreous of a human eye, for example through a 27 gauge needle. By reducing the viscosity of our formulation it can be injected into the vitreous through a 28, 29, or 30 gauge needle.

Preferably, the TKI component of the present pharmaceutical compositions comprise small molecules that are either soluble, or are substantially uniformly suspended in the composition, and the viscosity inducing component is a polymeric hyaluronate.

A detailed embodiment within the scope of our invention is a pharmaceutical composition for treating a posterior ocular condition, comprising a TKI component; polymeric hyaluronate, in which the TKI component is present; sodium chloride; sodium phosphate, and water. The pharmaceutical composition can have a viscosity at a shear rate of about 0.1/second of between about 80,000 cps to about 300,000 cps, preferably from about 100,000 cps to about 300,000 cps, and most preferably from about 180,000 cps to about 225,000 cps. Note that the pharmaceutical composition can have a viscosity at a shear rate of about 0.1/second of between about 80,000 cps and about 300,000 cps, and that when the pharmaceutical composition has a viscosity at a shear rate of about 0.1/second of between about 100,000 cps and about 150,000 cps it can be injected into the vitreous through a 27, 28, 29, or 30 gauge needle. Even with a 300,000 cps it is believed the present formulations can be injected through a 30 gauge needle due to shear thinning once the formulation is in movement in the syringe. The sodium phosphate present in the pharmaceutical composition can comprise both monobasic sodium phosphate and dibasic sodium phosphate. Additionally, the pharmaceutical composition can comprise an effective dose of a TKI component, between about 2% w/v hyaluronate and about 3% w/v hyaluronate, about 0.6% w/v sodium chloride and between about 0.03% w/v sodium phosphate and about 0.04% w/v sodium phosphate. Alternately, the pharmaceutical composition of claim 5 can comprise between about 0.5% w/v hyaluronate and about 6% w/v hyaluronate. If desired the hyaluronate can be heated (see Example 15) to decrease its molecular weight (and therefore its viscosity) in the formulation.

The pharmaceutical composition can also comprises between about 0.6% w/v sodium chloride to about 0.9% w/v sodium chloride. Generally, more sodium chloride is used in the formulation as less phosphate is used in the formulation, for example 0.9% sodium chloride can be used if no phosphate is present in the formulation, as in this manner the tonicity of the formulation can be adjusted to obtain the desired isotonicity with physiological fluid. The pharmaceutical composition can comprise between about 0.0% w/v sodium phosphate and 0.1% w/v sodium phosphate. As noted, more phosphate can be used in the formulation if less sodium chloride is present in the formulation so as to obtain a desired pH 7.4 buffering effect.

Although hyaluronate solutions containing water-insoluble (or sparingly soluble) steroids or other compounds have been proposed for intravitreal injection (and in particular for a controlled delivery administration due to the particulate nature of the steroids), it has not been at all clear that intravitreally administered hyaluronate solutions would be useful for TKIs generally or any particular TKI agent specifically. This is due in part to the limited maximum injection volume (about 100 μl) possible for intravitreal injection (which limits the maximum dosage possible), to the varying solubilities, chemistries, and specific activities of the various TKIs. Thus, for example, it is not obvious 1) any particular TKI (including peptide, aptamer and/or small molecule TKIs) would be soluble at all in HA, 2) for water soluble TKIs, that the advantages of HA as a carrier would pertain to a soluble molecule, 3) that any particular TKI would be insoluble in HA to the extent that it is capable of being formulated in granular or particulate form with the requisite specific activity to make a TKI-HA formulation medically advantageous, 4) that peptide or aptamer TKIs could be formulated to advantage in HA, and 5) with regard to specific TKI compounds, that HA formulations combined with these particular compounds would be therapeutically efficacious, having a high enough specific activity for intravitreal administration.

A more detailed embodiment within the scope of our invention is a pharmaceutical composition for treating a posterior ocular condition, the pharmaceutical composition consisting essentially of a TKI component, polymeric hyaluronate, in which polymeric hyaluronate the TKI component is soluble, sodium chloride, sodium phosphate, and water. The pharmaceutical composition can have a viscosity at a shear rate 0.1/second of between about 128,000 cps and about 225,000 cps and the sodium phosphate present in the pharmaceutical composition can be present as both monobasic sodium phosphate and dibasic sodium phosphate.

A further embodiment of OUT invention is a TKI formulation for treating a posterior ocular condition, consisting of a TKI component, polymeric hyaluronate, sodium chloride, dibasic sodium phosphate heptahydrate, monobasic sodium phosphate monohydrate, and water, wherein the composition has a viscosity at a shear rate 0.1/second of between about 128,000 cps and about 225,000 cps.

The invention also includes a method for treating a posterior ocular condition by administering (as by injecting) the pharmaceutical composition of claim 1 to the vitreous of a human or animal, thereby treating the posterior ocular condition. Thus, we have invented a method for treating macular edema, macular degeneration, diabetic retinopathy, and other intraocular diseases by administering to the vitreous of a human eye a pharmaceutical composition comprising a TKI component, and a hyaluronate, wherein the pharmaceutical composition having a viscosity at a shear rate 0.1/second of between about 128,000 cps and about 225,000 cps.

A pharmaceutical composition within the scope of our invention for treating a posterior ocular condition can, in certain embodiments, comprise a TKI component present in a therapeutically effective amount as a plurality of particles, a viscosity inducing component in an amount effective to increase the viscosity of the composition, and an aqueous carrier component, wherein the composition has a viscosity of at least about 10 cps at a shear rate of 0.1/second and is injectable into the vitreous of a human eye and wherein the pharmaceutical composition releases the TKI component slowly over a period of up to at least about 45 days after the intravitreal injection. This pharmaceutical composition can exhibit reduced generation of intraocular inflammation, no plume effect (that is no wide dispersion of the TKI component into the vitreous as soon as the TKI component is intravitreally injected), and cohesiveness (observed by the retention of the form of the TKI component gel for 30 weeks or longer after intravitreal injection of the TKI component gel formulation) upon intravitreal injection of the pharmaceutical composition.

Our invention encompasses a method for treating a posterior ocular condition, the method comprising the step of intravitreal administration of a sustained release pharmaceutical composition implant comprising a TKI component present in a therapeutically effective amount, a viscosity inducing component in an amount effective to increase the viscosity of the composition, and an aqueous carrier component, wherein the composition has a viscosity of at least about 10 cps at a shear rate of 0.1/second and is injectable into the vitreous of a human eye, and wherein the posterior ocular condition is treated for up to about 30 weeks by the TKI component of the present formulation. In this method the pharmaceutical composition can comprise a TKI component, polymeric hyaluronate, sodium chloride, sodium phosphate, and water. Additionally, the intravitreal administration can be injected through a 27 gauge needle into the vitreous of a human eye.

The invention also includes, when the TKI component is not entirely soluble in the aqueous carrier, a process for making a pharmaceutical composition by (a) mixing particles of the TKI component about 4 microns to about 8 microns in diameter with sodium chloride crystals, and about 35% to about 40% of the total volume of the water (water for injection) used to make the formulation; (b) heating the TKI component and sodium chloride mixture to a temperature between about 120° C. and about 140° C., thereby preparing a first part; (c) mixing a sodium phosphate and water, thereby preparing a second part; (d) dissolving sodium hyaluronate with a molecular weight between about 1.0 million Daltons and about 1.9 million Daltons in another about 35% to about 40% of the total water volume used to make the formulation, followed by sterile filtration after the dissolving; (e) lyophilization of the dissolved sodium hyaluronate; (f) reconstitution of the lyophilized, sterile sodium hyaluronate, thereby preparing a third part; and; (g) aseptically combining the first, second and third parts, thereby making a sterile, uniform triamcinolone pharmaceutical composition which is, an opaque white gel suspension suitable for intravitreal injection to treat an ocular condition. Water is added as needed (q.s) to make the desired gel suspension which is about 80% to about 90% by weight water.

DESCRIPTION

The present invention is based upon our discovery of TKI-containing formulations specifically designed for intraocular, for example intravitreal, injection or administration to treat various ocular conditions, such a macula edema. Our TKI formulations have numerous superior characteristics and advantages, including the following: (1) our formulations may be made to be free of preservatives and resuspension aids, such as benzyl alcohol and/or a polysorbate; (2) concomitantly, our formulations have a much reduced retinal and photoreceptor toxicity; (3) as well as being sterile and optionally preservative-free, our TKI formulations can provide extended therapeutic effects due to the viscosity of the formulation and the relatively slow diffusion of the TKI component therefrom, and when formulated as a suspension of particles, can provide sustained release of therapeutic amounts of the TKI over, for example, a period of months periods upon intravitreal injection of such formulations. Thus, our viscous TKI formulations can be characterized as sustained release implants; (4) intravitreal administration of our TKI formulations is substantially unassociated with an increased incidence of adverse events such as substantially elevated intraocular pressure, glaucoma, cataract and/an intraocular inflammation; (5) intravitreal administration of our TKI formulations is not associated with an increased incidence of adverse events such elevated intraocular pressure, glaucoma, cataract and/an intraocular inflammation as compared to currently used or known intraocular (e.g., intravitreal) use TKI formulations; (6) in certain embodiments, our formulations permit TKI particles or crystals to be slowly released (as they solubilize in the viscous fluid of the posterior chamber) from a relatively discrete unitary location, thereby avoiding the plume effect (rapid dispersion) characteristic of less viscous aqueous formulations upon intravitreal administration; (7) avoidance of plume formation or rapid dispersion upon intravitreal administration, which beneficially reduces visual field obscuration.

Advantage (3) above can be provided by particular characteristics of our formulations, such as suspension of the TKI component in one or more particular high molecular weight polymers which permit sustained release of the TKI component by the formation of ion pairing or reverse phase association therewith. Thus, the TKI is slowly related from its association with the gel.

Generally, the present invention provides compositions useful for placement, preferably by injection, into a posterior segment of an eye of a human or animal. Such compositions in the posterior, e.g., vitreous, of the eye are therapeutically effective against one or more conditions and/or diseases of the posterior of the eye, and/or one or more symptoms of such conditions and/or diseases of the posterior of the eye.

It is important to note that while preferably the compositions disclosed herein are preferably administered by intravitreal injection to treat a posterior ocular condition, our compositions can also be administered (as by injection) by other routes, such as for example subconjuctival, sub-tenon, periocular, retrobulbar, suprachoroidal, and/or intrascleral to effectively treat an ocular condition. Additionally, a sutured or refillable dome can be placed over the administration site to prevent or to reduce "wash out", leaching and/or diffusion of the active agent in a non-preferred direction.

Compositions within the scope of our invention can comprise a TKI component; a viscosity inducing component; and an aqueous carrier component. The compositions are advantageously ophthalmically acceptable. One of the important advantages of the present compositions is that they are more compatible with or less irritating or toxic to the tissues in the posterior segment of the eye, for example, the retina of the eye, relative to therapeutic compositions previously proposed for intravitreal injection into a posterior segment of an eye, for example, a composition sold under the trademark KENALOG®-40, which comprises the steroid triamcinolone. In particular, in certain embodiments the present compositions advantageously are substantially free of added preservative components or include effective preservative components which are more compatible with or less irritating or toxic to the posterior segment, e.g., retina, of the eye relative to benzyl alcohol, which is included in the KENALOG®-40 composition as a preservative.

As noted above, the present compositions include a TKI component. Such TKI component is present in the compositions in a therapeutically effective amount that is in an amount effective in providing a desired therapeutic effect in the eye into which the composition is placed. The TKI component is either soluble in the aqueous formulation or in certain embodiments is present in the composition in a plurality of particles. Any suitable TKI component may be employed in according to the present invention, provided it is at least sufficiently soluble in the vitreous humor to be able to administer a therapeutically effective is dose to the ocular tissue.

In those embodiments in which the TKI component is not fully soluble in the formulation (and is present as a suspension of particles), certain parameters are helpfully observed. The TKI component of these embodiments advantageously has a limited solubility in water, for example, at 25° C. For example, the TKI component preferably has a solubility in water at 25° C. of less than 10 mg/ml. Of course, the TKI component should be ophthalmically acceptable, that is, should have substantially no significant or undue detrimental effect of the eye structures or tissues; of course this will depend upon the dosage regimen and the time period of continuous exposure of the tissues of the posterior segment. One particularly useful characteristic of the presently useful TKI components is the ability of such component to reduce the extent of angiogenesis, particularly VEGF-associated angiogenesis, in the posterior segment of the eye into which the composition is placed caused by the result of one or more diseases and/or conditions in the posterior segment of the eye.

Examples of presently preferred TKI components include, without limitation, small molecules, such as those described in patents and patent applications listed above and incorporated by reference therein.

The TKI component advantageously is present in an amount of at least about 10 mg per ml of the composition. Depending on the solubility of the TKI component, the TKI may be present in the present compositions in an amount in the range of about 1% or less to about 5% or about 10% or about 20% or about 30% or more (w/v) of the composition, or about 0.2 mg per 100 µl or about 0.4 mg per 100 µl, or about 0.5 mg per 100 µl, or about 1.0 mg per 100 µl or about 2.0 mg per 100 µl, or about 4.0 mg per 100 µl, or about 5.0 mg per 100 µl, or about 6.0 mg per 100 µl, or about 7.0 mg per 100 µl, or about 8.0 mg per 100 µl, or about 11 mg per 100 µl, or about 20 mg per 100 µl, or about 40 mg per 100 µl, or about 60 mg per 100 µl, or about 80 mg per 100 µl. Providing relatively high concentrations or amounts of TKI component in the present compositions is beneficial in that reduced volumes and frequency of dosages of the composition may be required to be placed or injected into the posterior segment of the eye in order to provide the same amount or more TKI component in the posterior segment of the eye relative to compositions which include less than about 4% (w/v) of the TKI component. Thus, in one very useful embodiment, the present compositions include more than about 4% (w/v), for example at least about 5% (w/v), to about 10% (w/v) or about 20% (w/v) or about 30% (w/v) of the TKI component. Injection of 100 µL or more of a fluid into the vitreous can result in an excess of fluid in the vitreous with elevated intraocular pressure and leakage of the fluid from the vitreous then potentially occurring.

The viscosity inducing component is present in an effective amount in increasing, advantageously substantially increasing, the viscosity of the composition. Without wishing to limit the invention to any particular theory of operation, it is believed that increasing the viscosity of the compositions to values well in excess of the viscosity of water, for example, at least about 100 cps at a shear rate of 0.1/second, compositions which are highly effective for placement, e.g., injection, into the posterior segment of an eye of a human or animal are obtained. Along with the advantageous placement or injectability of the present compositions into the posterior segment, the relatively high viscosity of the present compositions are believed to enhance the ability of the present compositions to maintain the TKI component localized for a period of time within the posterior segment after intravitreal injection or placement. In the event that the composition comprises particles or crystals of the TKI component, the viscosity of the composition maintains the particles in substantially uniform suspension for prolonged periods of time, for example, for as long as 1 to 2 years, without requiring resuspension processing and thereby increasing the effective shelf life of the composition. The relatively high viscosity of the present compositions may also have an additional benefit of at least assisting the compositions to have the ability to have an increased amount or concentration of the TKI component, as discussed elsewhere herein.

Advantageously, the present compositions have viscosities of at least about 10 cps or at least about 100 cps or at least about 1000 cps, more preferably at least about 10,000 cps and still more preferably at least about 70,000 cps or more, for example up to about 200,000 cps or about 250,000 cps, or about 300,000 cps or more, at a shear rate of 0.1/second. The present compositions not only have the relatively high viscosity as noted above but also have the ability or are structured or formed to be effectively placeable, e.g., injectable, into a posterior segment of an eye of a human or animal, preferably through a 27 gauge needle, or even through a 30 gauge needle.

The presently useful viscosity inducing components preferably are shear thinning components in that as the present composition containing such a shear thinning viscosity inducing component is passed or injected into the posterior segment of an eye, for example, through a narrow space, such as 27 gauge needle, under high shear conditions the viscosity of the composition is substantially reduced during such passage. After such passage, the composition regains substantially its pre-injection viscosity.

Any suitable viscosity inducing component, for example, ophthalmically acceptable viscosity inducing component, may be employed in accordance with the present invention. Many such viscosity inducing components have been proposed and/or used in ophthalmic compositions used on or in the eye. The viscosity inducing component is present in an amount effective in providing the desired viscosity to the composition. Advantageously, (and depending on its properties and average molecular weight the viscosity inducing component is present in an amount in a range of about 0.5% or about 1.0% to about 5% or about 10% or about 20% (w/v) of the composition. The specific amount of the viscosity inducing component employed depends upon a number of factors including, for example and without limitation, the specific viscosity inducing component being employed, the molecular weight of the viscosity inducing component being employed, the viscosity desired for the present composition being produced and/or used and the like factors, such as shear thinning, biocompatibility and possible biodegradability of the compositions.

The viscosity inducing component preferably comprises a polymeric component and/or at least one viscoelastic agent, such as those materials which are useful in ophthalmic surgical procedures.

Examples of useful viscosity inducing components include, but are not limited to, hyaluronic acid (such as a polymeric hyaluronic acid), carbomers, polyacrylic acid, cellulosic derivatives, polycarbophil, polyvinylpyrrolidone, gelatin, dextrin, polysaccharides, polyacrylamide, polyvinyl alcohol, polyvinyl acetate, derivatives thereof and mixtures and copolymers thereof. In a particularly preferred embodiment the composition comprises a hyaluronic acid component, such as a polymeric hyaluronic acid component.

An average molecular weight of the presently useful viscosity inducing components may be in a range of about 10,000 Daltons or less to about 2 million Daltons or more. In one particularly useful embodiment, the molecular weight of the viscosity inducing component is in a range of about 100,000 Daltons or about 200,000 Daltons to about 1 million Daltons or about 1.5 million Daltons. Again, the molecular weight of the viscosity inducing component useful in accordance with the present invention, may vary over a substantial range based on the type of viscosity inducing component employed, and the desired final viscosity of the present composition in question, as well as, possibly one or more other factors. In one embodiment, two or more distinct molecular weight ranges of the viscosity inducing component may be used to increase the shear thinning attributes of the composition.

In one very useful embodiment, a viscosity inducing component is a polymeric hyaluronate component, for example, a metal hyaluronate component, preferably selected from alkali metal hyaluronates, alkaline earth metal hyaluronates and mixtures thereof and still more preferably selected from sodium or potassium hyaluronates, and mixtures thereof. The molecular weight is of such hyaluronate component (i.e. a polymeric hyaluronic acid) preferably is in a range of about 50,000 Daltons or about 100,000 Daltons to about 1.3 million Daltons or about 2 million Daltons. In one embodiment, the present compositions include a polymeric hyaluronate component in an amount in a range about 0.05% to about 0.5% (w/v). In a further useful embodiment, the hyaluronate component is present in an amount in a range of about 1% to about 4% (w/v) of the composition. In this latter case, the very high polymer viscosity forms a gel that slows particle sedimentation and diffusion of dissolved solutes upon injection in the eye. Such a composition may be marketed in pre-filled syringes since the gel cannot be easily removed by a needle and syringe from a bulk container. Pre-filled syringes have the advantages of convenience for the injector and the safety which results from less handling and the opportunity for error or contamination.

In certain embodiments it may be advantageous to employ a cross-linked hyaluronate composition, since cross-linking should significantly prolong the persistence of polymer matrix in the vitreous chamber.

The aqueous carrier component is advantageously ophthalmically acceptable and may include one or more conventional excipients useful in ophthalmic compositions. The present compositions preferably include a major amount of liquid water. The present compositions may be, and are preferably, sterile, for example, prior to being used in the eye.

The present compositions preferably include at least one buffer component in an amount effective to control and/or maintain the pH of the composition and/or at least one tonicity component in an amount effective to control the tonicity or osmolality of the compositions; preferably the tonicity and/or osmolality will be substantially isotonic to the vitreous humor. More preferably, the present compositions include both a buffer component and a tonicity component.

The buffer component and tonicity component may be chosen from those which are conventional and well known in the ophthalmic art. Examples of such buffer components include, but are not limited to, acetate buffers, citrate buffers, phosphate buffers, borate buffers and the like and mixtures thereof. Phosphate buffers are particularly useful. Useful tonicity components include, but are not limited to, salts, particularly sodium chloride, potassium chloride, mannitol and other sugar alcohols, and other suitable ophthalmically acceptably tonicity component and mixtures thereof.

The amount of buffer component employed preferably is sufficient to maintain the pH of the composition in a range of about 6 to about 8, more preferably about 7 to about 7.5. The amount of tonicity component employed preferably is sufficient to provide an osmolality to the present compositions in a range of about 200 to about 400, more preferably about 250 to about 350, mOsmol/kg respectively. Advantageously, the present compositions are substantially isotonic.

The present compositions may include one or more other components in amounts effective to provide one or more useful properties and/or benefits to the present compositions. For example, the present compositions may include effective amounts of preservative components, preferably such components which are more compatible with the tissue in the posterior segment of the eye into which the composition is placed than benzyl alcohol. Examples of such preservative components include, without limitation, benzalkonium chloride, chlorhexidine, PHMB (polyhexamethylene biguanide), methyl and ethyl parabens, hexetidine, chlorite components, such as stabilized chlorine dioxide, metal chlorites and the like, other ophthalmically acceptable preservatives and the like and mixtures thereof. The concentration of the preservative component, if any, in the present compositions is a concentration effective to preserve the composition, and is often in a range of about 0.00001% to about 0.05% or about 0.1% (w/v) of the composition.

Despite the previous paragraph, however, the present compositions are very preferably substantially free of added preservative components. In general, unit dose products need no preservative, but are pre-sterilized, for example, by heat or irradiation, prior to being packaged for use.

In addition, if the TKI component is in suspension in the composition, the present composition may include an effective amount of resuspension component effective to facilitate the suspension or resuspension of the TKI component particles in the present compositions. As noted above, in certain embodiments, the present compositions are free of added resuspension components. In other embodiments of the present compositions effective amounts of resuspension components are employed, for example, to provide an added degree of insurance that the TKI component particles remain in suspension, as desired and/or can be relatively easily resuspended in the present compositions, such resuspension be desired. Advantageously, the resuspension component employed in accordance with the present invention, if any, is chosen to be more compatible with the tissue in the posterior segment of the eye into which the composition is placed than polysorbate 80.

Any suitable resuspension component may be employed in accordance with the present invention. Examples of such resuspension components include, without limitation, surfactants such as poloxanes, for example, sold under the trademark PLURONIC®; tyloxapol; sarcosinates; polyethoxylated castor oils, other surfactants and the like and mixtures thereof.

One very useful class of resuspension components are those selected from vitamin derivatives. Although such materials have been previously suggested for use as surfactants in ophthalmic compositions, they have been found to be effective in the present compositions as resuspension components. Examples of useful vitamin derivatives include, without limitation, Vitamin E tocopheryl polyethylene glycol succinates, such as Vitamin E tocopheryl polyethylene glycol 1000 succinate (Vitamin E TPGS). Other useful vitamin derivatives include, again without limitation, Vitamin E tocopheryl polyethylene glycol succinamides, such as Vitamin E tocopheryl polyethylene glycol 1000 succinamide (Vitamin E TPGSA) wherein the ester bond between polyethylene glycol and succinic acid is replaced by an amide group.

The presently useful resuspension components are present, if at all, in the compositions in accordance with the present invention in an amount effective to facilitate suspending the particles in the present compositions, for example, during manufacture of the compositions or thereafter. The specific amount of resuspension component employed may vary over a wide range depending, for example, on the specific resuspension component being employed, the specific composition in which the resuspension component is being employed and the like factors. Suitable concentrations of the resuspension component, if any, in the present compositions are often in a range of about 0.01% to about 5%, for example, about 0.02% or about 0.05% to about 1.0% (w/v) of the composition.

Solubility of the TKI component is clearly important to the effectiveness of the present TKI-containing compositions, as is the potency and efficacy of the TKI components themselves. Very soluble TKI components are more readily and immediately available to the intraocular tissues, but may accordingly require smaller doses of the TKI component (and more frequent administration) to avoid substantially exceeding the effective dose. The viscosity of the present compositions will, to some extent, slow the diffusion of even these very soluble TKI components, but will not as effectively provide for an extended period of delivery and resulting efficacy as, for example is true when the TKI component is sequestered or somewhat insoluble (and thus solubilized over a period of time in situ) in the TKI composition of the present invention. The availability of minimally soluble TKI components, particularly small molecule TKI components, to intraocular tissues may be limited by the dissolution rate for these substances. As with readily soluble TKI components, slow dissolution is both good and bad for the patient. On the one hand, after a single intravitreal injection of the present composition, the mean elimination half-life for the TKI component is advantageously quite long. On the other hand, therapeutic drug levels in the vitreous compartment of the eye may not be achieved for some time (for example, about 1 to about 3 days), due to the slow dissolution rate of the TKI component particles.

In one embodiment of the present invention, for example, if a TKI component is not very soluble and particularly if the TKI component is both not very soluble and has a relatively high potency and/or efficacy, an effective amount of a solubilizing component is provided in the composition to solubilize a minor amount, that is less than 50%, for example in a range of 1% or about 5% to about 10% or about 20% of the TKI component. For example, the inclusion of a cyclodextrin component, such as β-cyclodextrin, sulfo-butylether β-cyclodextrin (SBE), other cyclodextrins and the like and mixtures thereof, at about 0.5 to about 5.0% (w/v) may solubilize about 1 to about 10% of the initial dose of the TKI component. This presolubilized fraction provides a readily bioavailable loading dose, thereby avoiding or minimizing delay time in achieving therapeutic effectiveness.

The use of such a solubilizing component is advantageous to provide any relatively quick "burst" release of an otherwise largely insoluble TKI component into the eye for therapeutic effectiveness. Such solubilizing component, of course, should be ophthalmically acceptable or at least sufficiently compatible with the posterior segment of the eye into which the composition is placed to avoid undue damage to the tissue in such posterior segment.

The pharmacokinetics of the TKI component following intravitreal administration may involve both the rate of drug dissolution and the rate of drug efflux via the anterior route. Patients typically require repeat dosing, for example about every two or three months, or otherwise as necessary.

In one embodiment of the present invention, the compositions further contain sustained release components, for example, polymers (in the form, for example, of gels and microspheres or nanospheres of between about 100 nm and about 200 nm in diameter), such as poly(D,L,-lactide) or poly(D,L-lactide co-glycolide), in amounts effective to reduce local diffusion rates and/or TKI particle dissolution rates. In particular embodiments, the TKI component is entrapped or sequestered by the solid insert during fabrication of the sustained release inserts or spheres. These particles can then be suspended or dispersed in high molecular weight hyaluronic acid. The result is a flatter elimination rate profile with a lower $C_{max}$ and a more prolonged therapeutic window, thereby extending the time between required injections for many patients.

Any suitable, preferably conditionally acceptable, release component may be employed. Useful examples are set forth above. The sustained release component is preferably biodegradable or bioabsorbable in the eye so that no residue remains over the long term. The amount of the delayed release component included may vary over a relatively wide range depending, for example, on the specific sustained release component is being employed, the specific release profile desired and the like factors. Typical amounts of delayed release components, if any, included in the present compositions are in a range of at least about 0.05 to 0.1 to about 0.5 or about 1 or more percent (w/v) (weight of the ingredient in the total volume of the composition) of the composition. In other embodiments, the sustained release components may be present in microspheres and nanoparticles containing the TKI component; in such compositions the sustained release component may be present in at least about 5%, or at least about 20%, or at least about 15%, or at least about 20%, or at least about 25%, or at least about 30%, or at least about 35%, or at least about 40%, or at least about 45%, or at least about 50% of the final composition. Preferably the TKI component is present in a concentration of about 1% to about 10%. All percentages listed here are weight percent.

The present compositions can be prepared using suitable blending/processing techniques or techniques, for example, one or more conventional blending techniques. The preparation processing should be chosen to provide the present compositions in forms which are useful for placement or injection into the posterior segments of eyes of humans or animals. Soluble TKI can be simply mixed with a hyaluronic acid solution. In one useful embodiment utilizing a somewhat insoluble, small molecule TKI component, a TKI component dispersion is made by combining the TKI component with water, and the excipient (other than the viscosity inducing component) to be included in the final composition. The ingredients are mixed to disperse the TKI component and then autoclaved. Alternatively, the TKI particles may be γ-irradiated or β-irradiated before addition to the sterile carrier. The viscosity inducing component may be purchased sterile or sterilized by conventional processing, for example, by filtering a dilute solution followed by lyophylization to yield a sterile powder. The sterile viscosity inducing component is combined with water to make an aqueous concentrate. Under aseptic conditions, the concentrated TKI component dispersion can be blended or mixed and added or combined as a slurry to the viscosity inducing component concentrate. Water is added in a quantity sufficient (q.s.) to provide the desired composition and the composition is mixed until homogenous.

Methods of using the present composition are provided and are included within the scope of the present invention. In general, such methods comprise administering a composition in accordance with the present invention to a posterior segment of an eye of a human or animal, thereby obtaining a desired therapeutic effect, such as treatment of a given condition of the anterior or posterior segment of the eye. The administering step advantageously comprises at least one of intravitreal injecting, subconjunctival injecting, sub-tenon injecting, retrobulbar injecting, suprachoroidal injecting and the like. A syringe apparatus including an appropriately sized needle, for example, a 27 gauge needle or a 30 gauge needle, can be effectively used to inject the composition with the posterior segment of an eye of a human or animal.

Ocular conditions which can be treated or addressed in accordance with the present invention include, without limitation, the following:

Maculopathies/retinal degeneration: macular degeneration, including age related macular degeneration (ARMD), such as non-exudative age related macular degeneration and exudative age related macular degeneration, choroidal neovascularization, retinopathy, including diabetic retinopathy, acute and chronic macular neuroretinopathy, central serous chorioretinopathy, and macular edema, including cystoid macular edema, and diabetic macular edema. Uveitis/retinitis/choroiditis: acute multifocal placoid pigment epitheliopathy, Behcet's disease, birdshot retinochoroidopathy, infectious (syphilis, lyme, tuberculosis, toxoplasmosis), uveitis, including intermediate uveitis (pars planitis) and anterior uveitis, multifocal choroiditis, multiple evanescent white dot syndrome (MEWDS), ocular sarcoidosis, posterior scleritis, serpignous choroiditis, subretinal fibrosis, uveitis syndrome, and Vogt-Koyanagi-Harada syndrome. Vascular diseases/exudative diseases: retinal arterial occlusive disease, central retinal vein occlusion, disseminated intravascular coagulopathy, branch retinal vein occlusion, hypertensive fundus changes, ocular ischemic syndrome, retinal arterial microaneurysms, Coat's disease, parafoveal telangiectasis, hemi-retinal vein occlusion, papillophlebitis, central retinal artery occlusion, branch retinal artery occlusion, carotid artery disease (CAD), frosted branch angitis, sickle cell retinopathy and other hemoglobinopathies, angioid streaks, familial exudative vitreoretinopathy, Eales disease. Traumatic/surgical: sympathetic ophthalmia, uveitic retinal disease, retinal detachment, trauma, laser, PDT, photocoagulation, hypoperfusion during surgery, radiation retinopathy, hone marrow transplant retinopathy. Proliferative disorders: proliferative vitreal retinopathy and epiretinal membranes, proliferative diabetic retinopathy. Infectious disorders: ocular histoplasmosis, ocular toxocariasis, presumed ocular histoplasmosis syndrome (POHS), endophthalmitis, toxoplasmosis, retinal diseases associated with HIV infection, choroidal disease associated with HIV infection, uveitic disease associated with HIV Infection, viral retinitis, acute retinal necrosis, progressive outer retinal necrosis, fungal retinal diseases, ocular syphilis, ocular tuberculosis, diffuse unilateral subacute neuroretinitis, and myiasis. Genetic disorders: retinitis pigmentosa, systemic disorders with associated retinal dystrophies, congenital stationary night blindness, cone dystrophies, Stargardt's disease and fundus flavimaculatus, Bests disease, pattern dystrophy of the retinal pigmented epithelium, X-linked retinoschisis, Sorsby's fundus dystrophy, benign concentric maculopathy, Bietti's crystalline dystrophy, pseudoxanthoma elasticum. Retinal tears/holes: retinal detachment, macular hole, giant retinal tear. Tumors: retinal disease associated with tumors, congenital hypertrophy of the RPE, posterior uveal melanoma, choroidal hemangioma, choroidal osteoma, choroidal metastasis, combined hamartoma of the retina and retinal pigmented epithelium, retinoblastoma, vasoproliferative tumors of the ocular fundus, retinal astrocytoma, intraocular lymphoid tumors. Miscellaneous: punctate inner choroidopathy, acute posterior multi focal placoid pigment epitheliopathy, myopic retinal degeneration, acute retinal pigment epithelitis and the like.

In preferred embodiments the present compositions include TKI components which comprise small molecules. Preferred TKIs are described in U.S. patent app Ser. Nos. 10/256,879 (U.S. Pub. No. 20030199478) and 10/259,703 (U.S. Pub. No. 20030225152), incorporated by reference herein.

In short, a TKI of the present viscous intraocular compositions include organic molecules capable of modulating, regulating and/or inhibiting tyrosine kinase signal transduction. Some compounds useful in the present implants are represented by the following formula:

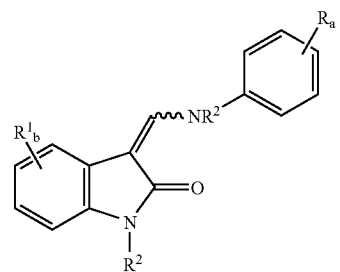

wherein $R^1$ is selected from the group consisting of halogen, $NO_2$, CN, $C_1$ to $C_4$ alkyl and aryl, e.g. phenyl; $R^2$ is selected from the group consisting of hydrogen, $C_1$ to $C_8$ alkyl, $COCH_3$, $CH_2CH_2OH$, $CH_2CH_2CH_2OH$ and phenyl; R is selected from the group consisting of D, halogen, $C_1$ to $C_8$ alkyl, $CF_3$, $OCF_3$, $OCF_2H$, $CH_2CN$, CN, $SR^2$, $(CR^7R^8)_cC(O)OR^2$, $C(O)N(R^2)_2$, $(CR^7R^8)_cOR^2$, $HNC(O)R^2$, $HN-C(O)OR^2$, $(CR^7R^8)_cN(R^2)_2$, $SO_2(CR^7R^8)_cN(R^2)_2$, $OP(O)(OR^2)_2$, $OC(O)OR^2$, $OCH_2O$, $HN-CH=CH$, $-N(COR^2)CH_2C_2$, $HC=N-NH$, $N=CH-S$, $O(CR^7R^8)_d-R^6$ and $(CR^7R^8)_n-R^6$, $-NR_2(CR^7R^8)_d-R^6$ wherein $R^6$ is selected from the group consisting of halogen, 3-fluoropyrrolidinyl, 3-fluoropiperidinyl, 2-pyridinyl, 3-pyridinyl, 4-pyridinyl, 3-pyrrolinyl, pyrrolidinyl, methyl isonipecotate, N-(2-methoxyethyl)-N-methylamyl, 1,2,3,6-tetrahydropyridinyl, morpholinyl, hexamethyleneiminyl, piperazinyl-2-one, piperazinyl, N-(2-methoxyethyl)ethylaminyl, thiomorpholinyl, heptamethyleneiminyl, 1-piperazinylcarboxaldehyde, 2,3,6,7-tetrahydro-(1H)-1,4-diazepinyl-5(4H)-one, N-methylhomopiperazinyl, (3-dimethylamino)pyrrolidinyl, N-(2-methoxyethyl)-N-propylaminyl, isoindolinyl, nipecotamidinyl, isonipecotamidinyl, 1-acetylpiperazinyl, 3-acetamidopyrrolidinyl, trans-decahydroisoquinolinyl, cis-decahydroisoquinolinyl, N-acetylhomopiperazinyl, 3-(diethylamino)pyrrolidinyl, 1,4-dioxa-8-azaspiro[4.5]decaninyl, 1-(2-methoxyethyl)-piperazinyl, 2-pyrrolidin-3-ylpyridinyl, 4-pyrrolidin-3-ylpyridinyl, 3-(methylsulfonyl)pyrrolidinyl, 3-picolylmethylaminyl, 2-(2-methylaminoethyl)pyridinyl, 1-(2-pyrimidyl)-piperazinyl, 1-(2-pyrazinyl)-piperazinyl, 2-methylaminomethyl-1,3-dioxolane,2-(N-methyl-2-aminoethyl)-1,3-dioxolane, 3-(N-acetyl-N-methylamino)pyrrolidiniyl, 2-methoxyethylaminyl, tetrahydrofurfurylaminyl, 4-aminotetrahydropyran, 2-amino-1-methoxybutane, 2-methoxyisopropylaminyl, 1-(3-aminopropyl)imidazole, histamyl, N,N-diisopropylethylenediaminyl, 1-benzyl-3- aminopyrrolidyl 2-(aminomethyl)-5-methylpyrazinyl, 2,2-dimethyl-1,3-dioxolane-4-methanaminyl, (R)-3-amino-1-N-BOC-pyrrolidinyl, 4-amino-1,2,2,6,6-pentamethylpiperidinyl, 4-aminomethyltetrahydropyran, ethanolamine and alkyl-substituted derivatives thereof and wherein when c is 1 said $CH_2$ may be

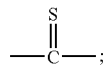

and $CH_2CH_2CH_2$; provided said alkyl or phenyl radicals may be substituted with one or two halo, hydroxy or lower alkyl amino radicals wherein $R^7$ and $R^8$ may be selected from the group consisting of H, F and $C_1$-$C_4$ alkyl or $CR^7R^8$ may represent a carbocyclic ring of from 3 to 6 carbons, preferably $R^7$ and $R^8$ are H or $CH_3$;

b is 0 or an integer of from 1 to 3;
a is 0 or an integer of from 1 to 5, preferably 1 to 3;
c is 0 or an integer of from 1 to 4,
d is an integer of from 2 to 5;
the wavy line represents a E or Z bond and pharmaceutically acceptable salts thereof.

In certain implants, the TKI is a compound having the foregoing formula, wherein $R^1$ is selected from the group consisting of H, i.e. b is 0; $CH_3$, F, Cl and phenyl.

Preferably, R is selected from the group consisting of $CH_3$, $CH_2CH_3$, $OCH_3$, OH, t-butyl, F, CN, $C(O)NH_2$, HN C(O)$CH_3$, $CH_2C(O)OH$, $SO_2NH_2$, C(O)OH, $OCF_2H$, isopropyl, $C_2H_5OH$, $C(O)OCH_3$, $CH_2OH$, NH—CH=CH, HC=N—N—H, N=CH—S, $O(CR^7R^8)_dR^6$, $(CR^7R^8)_cR^6$ and —$NR^2$$(CR^7R^8)_dR^6$, wherein $R^6$ is selected from the group consisting of 3-fluoropyrrolidinyl, 3-fluoropiperidinyl, 2-pyridinyl, 3-pyridinyl, 4-pyridinyl, 3-pyrrolinyl, pyrrolidinyl, methyl isonipecotate, N-(2-methoxyethyl)-N-methylamyl, 1,2,3,6-tetrahydropyridinyl, morpholinyl, hexamethyleneiminyl, piperazinyl-2-one, piperazinyl, N-(2-methoxyethyl)ethylaminyl, thiomorpholinyl, heptamethyleneiminyl, 1-piperazinylcarboxaldehyde, 2,3,6,7-tetrahydro-(1H)-1,4-diazepinyl-5(4H)-one. N-methylhomopiperazinyl, (3-dimethylamino)pyrrolidinyl, N-(2-methoxyethyl)-N-propylaminyl, isoindolinyl, nipecotamidinyl, isonipecotamidinyl, 1-acetylpiperazinyl, 3-acetamidopyrrolidinyl, trans-decahydroisoquinolinyl, cis-decahydroisoquinolinyl, N-acetylhomopiperazinyl, 3-(diethylamino)pyrrolidinyl, 1,4-dioxa-8-azaspiro[4.5]decaninyl, 1-(2-methoxyethyl)-piperazinyl, 2-pyrrolidin-3-ylpyridinyl, 4-pyrrolidin-3-ylpyridinyl, 3-(methylsulfonyl)pyrrolidinyl, 3-picolylmethylaminyl, 2-(2-methylaminoethyl)pyridinyl, 1-(2-pyrimidyl)-piperazinyl, 1-(2-pyrazinyl)-piperazinyl, 2-methylaminomethyl-1,3-dioxolane, 2-(N-methyl-2-aminoethyl)-1,3-dioxolane, 3-(N-acetyl-N-methylamino)pyrrolidinyl, 2-methoxyethylaminyl, tetrahydrofurylaminyl, 4-aminotetrahydropyran, 2-amino-1-methoxybutane, 2-methoxyisopropylaminyl, 1-(3-aminopropyl)imidazole, histamyl, N,N-diisopropylethylenediaminyl, 1-benzyl-3-aminopyrrolidyl 2-(aminomethyl)-5-methylpyrazinyl, 2,2-dimethyl-1,3-dioxolane-4-methanaminyl, (R)-3-amino-1-N-BOC-pyrrolidinyl, 4-amino-1,2,2,6,6-pentamethylpiperidinyl, 4-aminomethyltetrahydropyranyl, ethanolamine and alkyl-substituted derivatives thereof, e.g. $R^6$ is morpholinyl or $CH_2N(CH_3)_2$.

More preferably, R is selected from the group consisting of m-ethyl, p-methoxy, p-hydroxy, m-hydroxy, p-cyano, m-C(O)$NH_2$, p-HNC(O)$CH_3$, p-$CH_2C(O)OH$, p-$SO_2NH_2$, p-$CH_2OH$, m-methoxy, p-$CH_2CH_2CH_2OH$, HNCH=CH, HC=N—NH, p-morpholinyl, N—CH—S, p-$OCHF_2$, p-COOH, p-$CH_3$, p-$OCH_3$, m-F, m-$CH_2N(C_2H_3)_2$, $(CR^7R^8)_c$$R^6$, $O(CR^7R^8)_dR^6$ and $NR^2(CR^7R^8)_dR^6$.

It is noted that R may represent a condensed ring that is attached to the above phenyl ring at two positions. For example, $CH_2CH_2CH_9$ may be attached at the 3 and 4 (or m and p) positions of the phenyl ring.

Still more preferably, R is selected from the group consisting of fluoro, methyl, $(CR^7R^8)R^6$, $O(CR^7R^8)_dR^6$ and $NR^2$$(CR^7R^8)_dR^6$ wherein $R^6$ is selected from dimethylamino, diethylamino, 3-fluoropyrrolidinyl, 3-fluoropiperidinyl, 3-pyridinyl, 4-pyridinyl, pyrrolidinyl, morpholinyl, piperazinyl, heptamethyleneiminyl, tetrahydrofurylaminyl, 4-aminotetrahydropyranyl, N,N-diisopropylethylenediaminyl and 4-aminomethyltetrahydropyran.

In particular, the compounds of the present implants may be selected from the compounds of the tables below.

TABLE 1

| | | R Substitution | | | | |
|---|---|---|---|---|---|---|
| Compound # | $R^1$ | 2 | 3 | 4 | 5 | 6 |

Unsubstituted 4-Methyl & 5-Chloro-3-[(Substituted Phenylamino)-methylene]-1,3-dihydro-indol-2-ones.

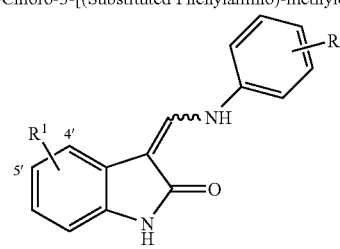

| | | | | | | |
|---|---|---|---|---|---|---|
| 1 | H | H | H | H | H | H |
| 2 | H | H | Br | H | H | H |
| 3 | H | H | H | Br | H | H |
| 4 | H | Br | H | H | H | H |
| 5 | H | H | H | Et | H | H |
| 6 | H | H | Et | H | H | H |
| 7 | H | H | H | OMe | H | H |
| 8 | H | H | H | $CO_2Et$ | H | H |
| 9 | H | Et | H | H | H | H |

TABLE 1-continued

| Compound # | R¹ | 2 | 3 | 4 | 5 | 6 |
|---|---|---|---|---|---|---|
| 10 | H | H | F | Me | H | H |
| 11 | H | Me | F | H | H | H |
| 12 | H | H | H | OH | H | H |
| 13 | H | H | Cl | OH | H | H |
| 14 | H | Me | H | F | H | H |
| 15 | H | H | OH | H | H | H |
| 16 | H | H | OMe | H | OMe | H |
| 17 | H | H | H | tBu | H | H |
| 18 | H | H | H | Me | H | H |
| 19 | H | H | Me | H | Me | H |
| 20 | H | H | Me | Me | H | H |
| 21 | H | H | F | OMe | H | H |
| 22 | H | H | CF₃ | H | H | H |
| 23 | H | H | —CH₂CH₂CH₂— | | H | H |
| 24 | H | F | H | Cl | H | H |
| 25 | H | H | H | CF₃ | H | H |
| 26 | H | F | H | Me | OCO₂Et | H |
| 27 | H | F | H | Me | OCO₂CH₂C(CH₃)₃ | H |
| 28 | H | F | H | Cl | OH | H |
| 29 | H | H | H | CN | H | H |
| 30 | H | H | H | CH₂CN | H | H |
| 31 | H | H | —CH=CH—NH— | | H | H |
| 32 | H | H | —NH—N=CH— | | H | H |
| 33 | H | H | H | CONH₂ | H | H |
| 34 | H | H | H | NHCOCH₃ | H | H |
| 35 | H | H | CH₂CO₂H | H | H | H |
| 36 | H | H | H | Cl | H | H |
| 37 | H | H | CO₂H | Cl | H | H |
| 38 | H | H | H | SO₂NH₂ | H | H |
| 39 | H | H | H | SO₂NHCOCH₃ | H | H |
| 40 | H | H | H | N-morpholino | H | H |
| 41 | H | H | H | OPh | H | H |
| 42 | H | H | OMe | OMe | H | H |
| 43 | H | H | —S—CH=N— | | H | H |
| 44 | H | H | OH | CO₂H | H | H |
| 45 | H | H | CF₃ | Cl | H | H |
| 46 | H | H | CF₃ | H | CF₃ | H |
| 47 | H | H | CF₃ | F | H | H |
| 48 | H | H | OH | Me | H | H |
| 49 | H | H | OH | OMe | H | H |
| 50 | H | H | H | OCHF₂ | H | H |
| 51 | H | H | H | OCF₃ | H | H |
| 52 | H | H | H | iPr | H | H |
| 53 | H | F | H | Me | H | H |
| 54 | H | H | Me | Cl | H | H |
| 55 | H | H | CF₃ | OMe | H | H |
| 56 | H | H | CF₃ | Me | H | H |
| 57 | 5'-Cl | H | OMe | H | H | H |
| 58 | 4'-Me | H | H | H | H | H |
| 59 | 4'-Me | H | H | OMe | H | H |
| 60 | 4'-Me | H | OH | H | H | H |
| 61 | 4'-Me | H | OMe | H | OMe | H |
| 62 | 4'-Me | H | H | Me | H | H |
| 63 | 4'-Me | H | Me | H | Me | H |
| 64 | 5'-Cl | H | H | OCHF₂ | H | H |
| 65 | 5'-Cl | H | OH | OMe | H | H |
| 66 | 5'-Cl | H | H | OCF₃ | H | H |
| 67 | 5'-Cl | H | Me | OH | H | H |
| 68 | 5'-Cl | H | —OCH₂O— | | H | H |
| 69 | 5'-Cl | H | Me | Me | H | H |
| 70 | 5'-Cl | H | H | iPr | H | H |
| 71 | 5'-Cl | H | OH | Me | H | H |
| 72 | 5'-Cl | H | H | (CH₂)₂OH | H | H |
| 73 | 5'-Cl | H | H | OMe | H | H |
| 74 | 5'-Cl | H | H | H | H | H |
| 75 | 5'-Cl | H | OMe | H | OMe | H |
| 76 | 5'-Cl | H | OH | H | H | H |
| 77 | 5'-Cl | H | H | OH | H | H |
| 78 | 5'-Cl | H | Me | H | Me | H |
| 79 | 5'-Cl | H | H | Me | H | H |

TABLE 1-continued

| Compound # | $R^1$ | R Substitution | | | | |
|---|---|---|---|---|---|---|
| | | 2 | 3 | 4 | 5 | 6 |
| 80 | H | H | —OCH$_2$O— | | H | H |
| 81 | H | H | CO$_2$H | OH | H | H |
| 82 | H | H | H | OEt | H | H |
| 83 | H | H | —N(COMe)—CH$_2$—CH$_2$— | | H | H |
| 84 | H | H | H | OPO(OH)$_2$ | H | H |
| 85 | H | H | CO$_2$H | CO$_2$H | H | H |
| 86 | H | H | H | CO$_2$H | H | H |
| 87 | H | H | H | (CH$_2$)$_2$OH | H | H |
| 88 | H | H | H | CH$_2$OH | H | H |
| 89 | H | H | OMe | CO$_2$CH$_3$ | H | H |
| 90 | 4'-Me | H | —NH—N=CH— | | H | H |
| 91 | 4'-Me | H | F | OMe | H | H |
| 92 | 4'-Me | H | —S—CH=N— | | H | H |
| 93 | 4'-Me | H | OMe | CO$_2$CH$_3$ | H | H |
| 94 | H | H | OMe | H | H | H |
| 95 | 4'-Me | H | Me | Me | H | H |
| 96 | 4'-Me | H | H | OH | H | H |
| 97 | 4'-Me | H | —CH=CH—NH— | | H | H |
| 98 | 4'-Me | H | H | t-Bu | H | H |
| 99 | 4'-Me | H | H | CH$_2$OH | H | H |
| 100 | 5'-Cl | H | H | t-Bu | H | H |
| 101 | 5'-Cl | H | —S—CH=N— | | H | H |
| 102 | 5'-Cl | H | OMe | OMe | H | H |
| 103 | 5'-Cl | H | —NH—N=CH— | | H | H |
| 104 | 5'-Cl | OMe | H | Cl | OMe | H |
| 105 | 5'-Cl | H | F | OMe | H | H |
| 106 | 5'-Cl | H | H | N-morpholino | H | H |
| 107 | 5'-Cl | H | H | OEt | H | H |
| 108 | 5'-Cl | H | CO$_2$H | OH | H | H |
| 109 | 5'-Cl | H | CH$_2$NEt$_2$ | OH | H | H |
| 110 | 5'-Cl | H | —CH=CH—NH— | | H | H |
| 111 | 5'-Cl | H | H | CH$_2$OH | H | H |
| 112 | 5'-Cl | H | Me | iPr | H | H |
| 113 | 4'-Me | H | H | CH$_2$CH$_2$OH | H | H |
| 114 | 5'-Cl | H | H | NHCOMe | H | H |
| 115 | 5'-Cl | H | H | CH$_2$CO$_2$H | H | H |
| 116 | 5'-Cl | H | H | SO$_2$NH$_2$ | H | H |
| 117 | 4'-Me | H | OH | OMe | H | H |
| 118 | 4'-Me | H | CO$_2$H | OH | H | H |
| 119 | 4'-Me | H | H | OCHF$_2$ | H | H |
| 120 | 4'-Me | H | H | OCF$_3$ | H | H |
| 121 | 4'-Me | H | CF$_3$ | OMe | H | H |
| 122 | 4'-Me | H | H | OEt | H | H |
| 123 | 4'-Me | H | H | iPr | H | H |
| 124 | 4'-Me | H | —O—CH$_2$—O— | | H | H |
| 125 | 4'-Me | H | OH | Me | H | H |
| 126 | 4'-Me | H | OMe | OMe | H | H |
| 127 | 4'-Me | Et | H | H | H | H |
| 128 | 4'-Me | H | H | CN | H | H |
| 129 | 4'-Me | H | H | CONH$_2$ | H | H |
| 130 | 4'-Me | H | H | NHCOCH$_3$ | H | H |
| 131 | 4'-Me | H | H | CH$_2$CO$_2$H | H | H |
| 132 | 4'-Me | H | Me | OH | H | H |
| 133 | H | H | Me | OH | H | H |
| 134 | H | H | OH | NHCO$_2$Et | H | H |
| 135 | 4'-Me | F | H | OMe | H | H |
| 136 | H | H | H | SMe | H | H |
| 137 | 4'-Me | H | H | SMe | H | H |
| 138 | 5'-Cl | H | H | SMe | H | H |
| 139 | H | H | H | —CH$_2$CH$_2$CH$_2$CO$_2$H | H | H |
| 140 | 4'-Me | H | H | —CH$_2$CH$_2$CH$_2$CO$_2$H | H | H |
| 141 | H | H | —CH$_2$CH$_2$CO$_2$H | H | H | H |
| 142 | 4'-Me | H | —CH$_2$CH$_2$CO$_2$H | H | H | H |
| 143 | 5'-Cl | H | —CH$_2$CH$_2$CO$_2$H | H | H | H |
| 144 | H | H | H | —CH$_2$CH$_2$CO$_2$H | H | H |
| 145 | 4'-Me | H | H | —CH$_2$CH$_2$CO$_2$H | H | H |
| 146 | 5'-Cl | H | H | —CH$_2$CH$_2$CO$_2$H | H | H |

TABLE 1-continued

Unsubstituted, 4-methyl, 5-Chloro & 5-Fluoro 3-[(Substituted Phenylamino)-methyl]-1,3-dihydro-indol-2-ones.

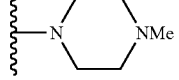

| Compound # | R¹ | 2 | 3 | 4 | 5 | 6 |
|---|---|---|---|---|---|---|
| 147 | 4'-Me | H | Et | H | H | H |
| 148 | 5'-Cl | H | Et | H | H | H |
| 149 | 5'-Cl | H | H | Et | H | H |
| 150 | 5'-Cl | H | H | —CH₂CH₂CH₂CO₂H | H | H |
| 151 | 4'-Me | H | H | Et | H | H |
| 152 | 5'-Cl | H | H | —CN | H | H |
| 155 | 4'-Me | H | OH | CO₂H | H | H |
| 156 | H | H | H | N(Me)₂ | H | H |
| 157 | H | H | H | 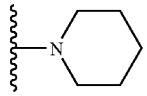 | H | H |
| 158 | H | H | H | 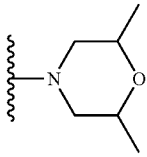 [SMILES: *N1CC(C)OC(C)C1] | H | H |
| 159 | H | H | H | 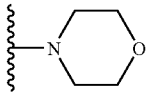 | H | H |
| 160 | H | H | CH₂N(Et)₂ | OH | H | H |
| 161 | 4'-Me | H | CH₂N(Et)₂ | OH | H | H |
| 162 | 5'-F | H | —CH=CH—NH— | | H | H |
| 163 | 5'-F | H | —NH—N=CH— | | H | H |
| 164 | 5'-F | H | OH | OMe | H | H |
| 165 | 5'-F | H | H | CH₂CH₂CO₂H | H | H |
| 166 | 5'-F | H | H | SO₂NH₂ | H | H |
| 167 | 5'-F | H | H |  | H | H |
| 168 | 5'-F | H | H | 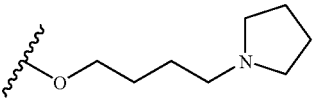 [SMILES: *OCCCCN1CCCC1] | H | H |
| 169 | 5'-F | H | H | H | H | H |
| 170 | 5'-F | H | H | CONH₂ | H | H |
| 171 | 5'-F | H | H | SMe | H | H |
| 172 | 5'-F | H | F | OMe | H | H |
| 173 | 5'-F | H | —S—CH=N— | | H | H |
| 174 | 5'-F | H | H | CH₂CO₂H | H | H |
| 175 | 5'-F | H | CH₂CH₂CO₂H | H | H | H |
| 176 | 5'-F | H | Et | H | H | H |
| 177 | 5'-F | H | OH | H | H | H |
| 178 | 5'-F | H | H | CH₂OH | H | H |
| 179 | H | H | H | (pyrrolidinyl-butoxy group) | H | H |

TABLE 1-continued

| Compound # | R¹ | 2 | 3 | 4 | 5 | 6 |
|---|---|---|---|---|---|---|
| 180 | H | H | H | NH₂ | H | H |
| 181 | 4'-Me | H | H | NH₂ | H | H |
| 182 | H | H | CH(OH)CH₃ | H | H | H |
| 183 | 4'-Me | H | CH(OH)CH₃ | H | H | H |
| 184 | H | H | CH₂OH | H | H | H |
| 185 | 4'-Me | H | CH₂OH | H | H | H |
| 186 | H | H | NHCO₂t-Bu | H | H | H |
| 187 | 4'-Me | H | NHCO₂t-Bu | H | H | H |
| 188 | H | H | H | N(Et)₂ | H | H |
| 189 | 4'-Me | H | H | N(Et)₂ | H | H |
| 190 | H | H | SO₂N(CH₂CH₂OH)₂ | H | H | H |
| 191 | 4'-Me | H | SO₂N(CH₂CH₂OH)₂ | H | H | H |
| 192 | H | H | H | SO₂NCH₂CH₂OH | H | H |
| 193 | H | H | SO₂NCH₂CH₂CH₂OH | H | H | H |
| 194 | 4'-Me | H | SO₂NCH₂CH₂CH₂OH | H | H | H |
| 195 | H | H | CO₂H | 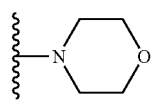 | H | H |
| 196 | 4'-Me | H | H | 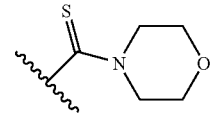 | H | H |
| 197 | 4'-Me | H | H | SO₂NCH₂CH₂OH | H | H |
| 198 | H | H | H | OCH₂CH₂CH₂Cl | H | H |
| 199 | H | H | H | OCH₂CH₂CH₂CH₂Cl | H | H |
| 200 | H | H | H | OCH₂CH₂CH₂I | H | H |
| 201 | H | H | H | OCH₂CH₂CH₂CH₂I | H | H |
| 202 | 4'-Me | D | D | D | D | D |
| 203 | H | D | D | CO₂H | D | D |
| 204 | H | D | D | NH₂ | D | D |
| 205 | 4'-Me | D | D | NH₂ | D | D |
| 206 | H | H | H | 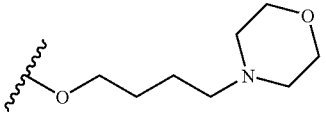 [SMILES: *OCCCCN1CCOCC1] | H | H |
| 207 | H | H | H | OCH₂CH₂CH₂CH₂N(Et)₂ | H | H |
| 208 | H | H | H | 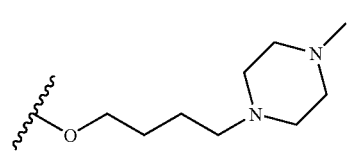 [SMILES: *OCCCCN1CCN(C)CC1] | H | H |
| 209 | H | H | H | 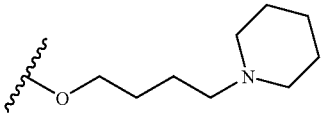 [SMILES: *OCCCCN1CCCCC1] | H | H |
| 210 | 4'-Me | H | NH₂ | H | H | H |
| 211 | H | H | NH₂ | H | H | H |
| 212 | H | H | NH₂ | Me | H | H |
| 213 | 4'-Me | H | NH₂ | Me | H | H |
| 214 | H | H | H | OCH₂CH₂CH₂N(Et)₂ | H | H |
| 215 | H | H | H | 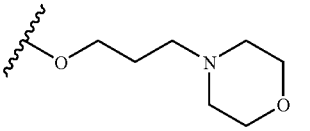 [SMILES: *OCCCN1CCOCC1] | H | H |

TABLE 1-continued
| Compound # | R¹ | 2 | 3 | 4 | 5 | 6 |
|---|---|---|---|---|---|---|
| 216 | H | H | H | 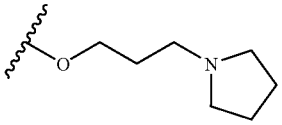 [SMILES: *OCCCN1CCCC1] | H | H |
| 217 | H | H | H | 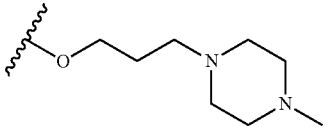 [SMILES: *OCCCN1CCN(C)CC1] | H | H |
| 218 | H | H | H | 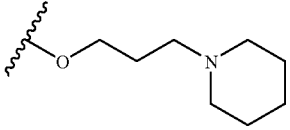 [SMILES: *OCCCN1CCCCC1] | H | H |
| 219 | 5'-F | H | H | 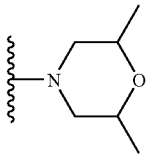 [SMILES: *N1CC(C)OC(C)C1] | H | H |
| 220 | 4'-Me | H | H | 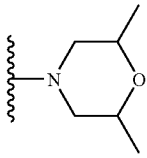 | H | H |
Unsubsituted, 4-Fluoro, 4-methyl, 5-Chloro, 5-Cyano, 5-Fluoro, 5-Nitro, 6-Fluoro & 6-Aryl 3-[(Substituted Phenylamino)-methylene]-1,3-dihydro-indol-2-ones.
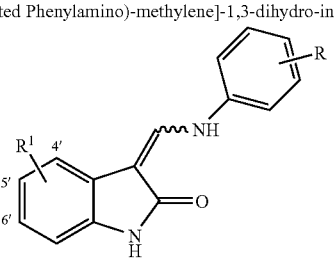
| Compound # | R¹ | 2 | 3 | 4 | 5 | 6 |
|---|---|---|---|---|---|---|
| 221 | 5'-F | H | H | 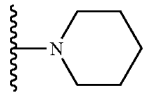 | H | H |
| 222 | 5'-F | H | H | OMe | H | H |
| 223 | H | D | D | D | D | D |
| 224 | H | H | H | CH₂CO₂H | H | H |
| 225 | H | H | H |  | H | H |
| 226 | H | H | H |  | H | H |

TABLE 1-continued
| Compound # | R¹ | 2 | 3 | 4 | 5 | 6 |
|---|---|---|---|---|---|---|
| 227 | 4'-Me | H | H | 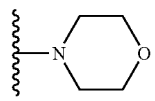 | H | H |
| 228 | 6'-F | H | H | 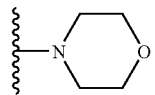 | H | H |
| 229 | 6'-F | H | H | 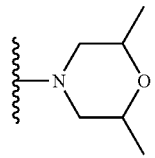 | H | H |
| 230 | 6'-F | H | H | 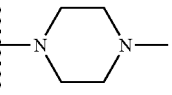 | H | H |
| 231 | 4'-Me | H | H | 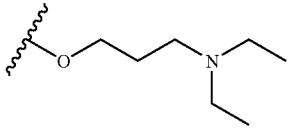 [SMILES: *OCCCN(CC)CC] | H | H |
| 232 | 5'-Cl | H | H | 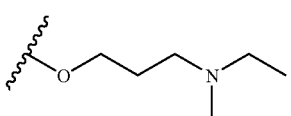 | H | H |
| 233 | 5'-F | H | H | 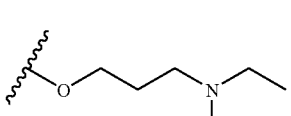 | H | H |
| 234 | 6'-F | H | H | 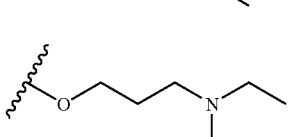 | H | H |
| 235 | H | H | H | 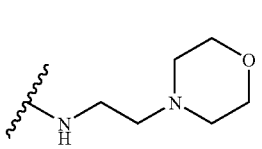 | H | H |
| 236 | 5'-NO₂ | H | H | 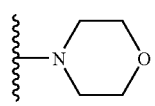 | H | H |
| 237 | 5'-CN | H | H | 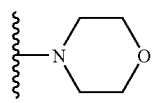 | H | H |

TABLE 1-continued
| Compound # | R¹ | 2 | 3 | 4 | 5 | 6 |
|---|---|---|---|---|---|---|
| 238 | 4'-Me | H | H | 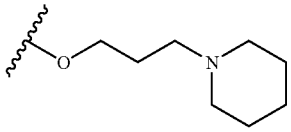 [SMILES: *OCCCN1CCCCC1] | H | H |
| 239 | 6'-F | H | H | 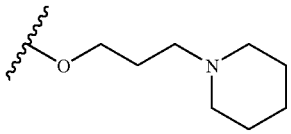 [SMILES: *OCCCN1CCCCC1] | H | H |
| 240 | 5'-F | H | H | 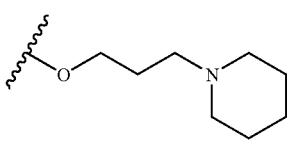 | H | H |
| 241 | 5'-Cl | H | H | 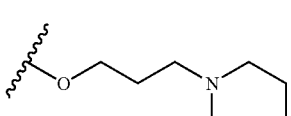 | H | H |
| 242 | 4'-Me | H | H | 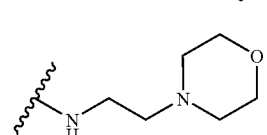 | H | H |
| 243 | 6'-F | H | H | 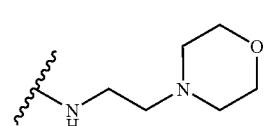 | H | H |
| 244 | 5'-F | H | H | 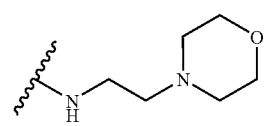 | H | H |
| 245 | 5'-Cl | H | H | 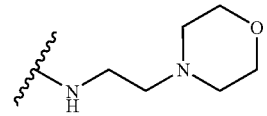 [SMILES: *NCCN1CCOCC1] | H | H |
| 246 | 4'-Me | H | H | 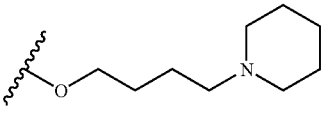 [SMILES: *OCCCCN1CCCCC1] | H | H |
| 247 | 6'-F | H | H | 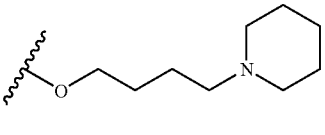 [SMILES: *OCCCCN1CCCCC1] | H | H |
| 248 | H | H | F | 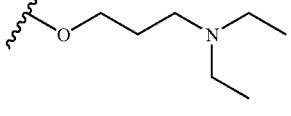 | H | H |

TABLE 1-continued
| Compound # | R¹ | 2 | 3 | 4 | 5 | 6 |
|---|---|---|---|---|---|---|
| 249 | 4'-Me | H | F | 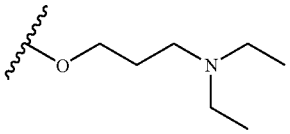 | H | H |
| 250 | 6'-F | H | F | 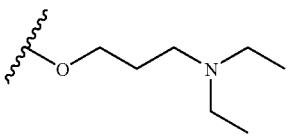 | H | H |
| 251 | H | H | H | 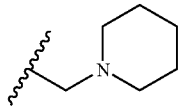 [SMILES: *CN1CCCCC1] | H | H |
| 252 | 4'-Me | H | H | 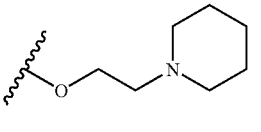 [SMILES: *OCCN1CCCCC1] | H | H |
| 253 | 6'-F | H | H | 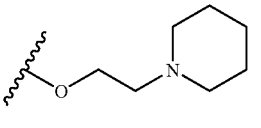 [SMILES: *OCCN1CCCCC1] | H | H |
| 254 | H | H | H | 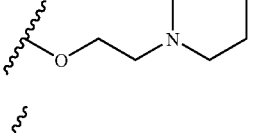 | H | H |
| 255 | 4'-F | H | H | 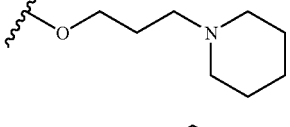 | H | H |
| 256 | 4'-Me | H | H | 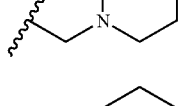 | H | H |
| 257 | 4'-F | H | H | 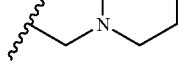 | H | H |
| 258 | 5'-F | H | H | 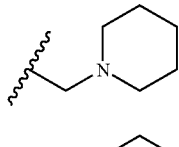 | H | H |
| 259 | 6'-F | H | H | 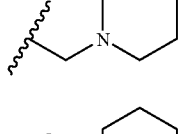 | H | H |
| 260 | 5'-Cl | H | H | 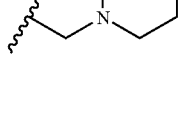 | H | H |

TABLE 1-continued
| Compound # | R¹ | 2 | 3 | 4 | 5 | 6 |
|---|---|---|---|---|---|---|
| 261 | 4'-F | H | H | 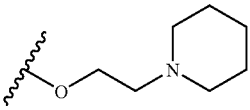 | H | H |
| 262 | 5'-Cl | H | H | 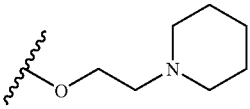 [SMILES: *OCCN1CCCCC1] | H | H |
| 263 | 5'-F | H | H | 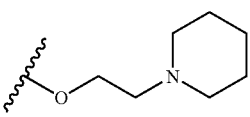 [SMILES: *OCCN1CCCCC1] | H | H |
| 264 | 4'-Me | H | H | 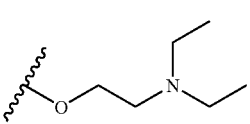 [SMILES: *OCCN(CC)CC] | H | H |
| 265 | H | H | H |  | H | H |
| 266 | 6'-F | H | H |  | H | H |
| 267 | 4'-F | H | H | 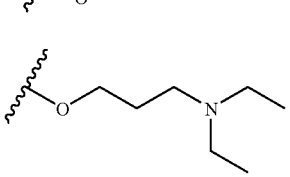 | H | H |
| 268 | 6'-(3-Methoxyphenyl) | H | H | 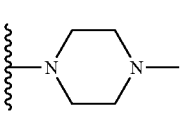 | H | H |
| 269 | 6'-(3-Methoxyphenyl) | H | H | 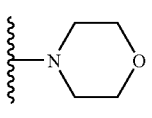 | H | H |
| 270 | 4'-Me | H | H | 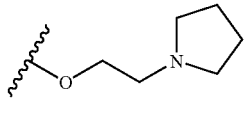 [SMILES: *OCCN1CCCC1] | H | H |
| 271 | 6'-F | H | H | 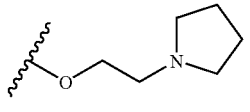 [SMILES: *OCCN1CCCC1] | H | H |
| 272 | H | H | H | 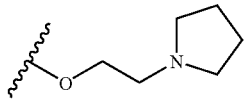 [SMILES: *OCCN1CCCC1] | H | H |

TABLE 1-continued
| Compound # | R¹ | 2 | 3 | 4 | 5 | 6 |
|---|---|---|---|---|---|---|
| 273 | 4'-F | H | H | 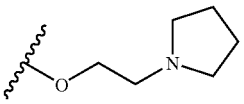 [SMILES: *OCCN1CCCC1] | H | H |
| 274 | 5'-F | H | H | 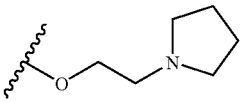 [SMILES: *OCCN1CCCC1] | H | H |
| 275 | 5'-Cl | H | H | 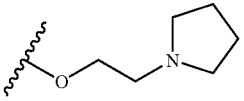 [SMILES: *OCCN1CCCC1] | H | H |
| 276 | 6'-(3-Methoxyphenyl) | H | H | 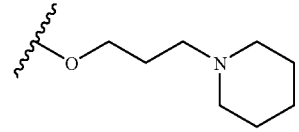 [SMILES: *OCCCN1CCCCC1] | H | H |
| 277 | 6'-(3-Methoxyphenyl) | H | H | 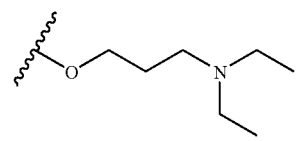 [SMILES: *OCCCN(CC)CC] | H | H |
| 278 | 4'-Me | H | H | 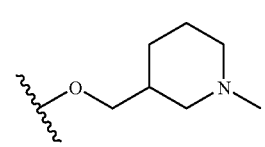 [SMILES: *OCC1CCCN(C)C1] | H | H |
| 279 | 6'-F | H | H | 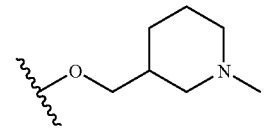 | H | H |
| 280 | H | H | H | 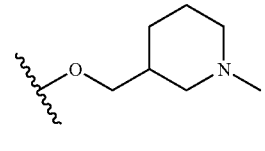 [SMILES: *OCC1CCCN(C)C1] | H | H |
| 281 | 4'-F | H | H | 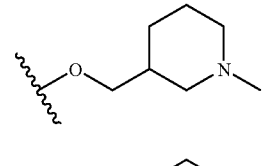 | H | H |
| 282 | 5'-F | H | H | 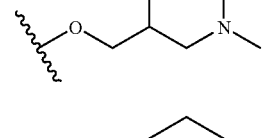 | H | H |
| 283 | 5'-Cl | H | H | 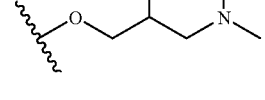 | H | H |

TABLE 1-continued
| Compound # | R¹ | 2 | 3 | 4 | 5 | 6 |
|---|---|---|---|---|---|---|
| 284 | H | H | H | 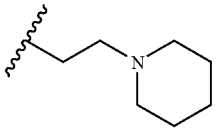 [SMILES: *CCN1CCCCC1] | H | H |
| 285 | 5'-Cl | H | H | 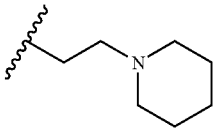 [SMILES: *CCN1CCCCC1] | H | H |
| 286 | 4'-Me | H | H | 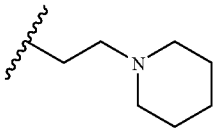 [SMILES: *CCN1CCCCC1] | H | H |
| 287 | 4'-F | H | H | 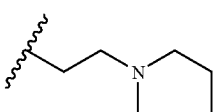 | H | H |
| 288 | 5'-F | H | H | 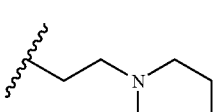 | H | H |
| 289 | 6'-F | H | H | 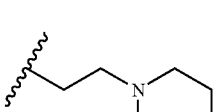 | H | H |
| 290 | H | H | H | 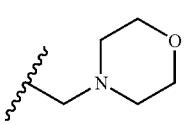 [SMILES: *CN1CCOCC1] | H | H |
| 291 | 5'-Cl | H | H | 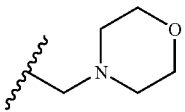 | H | H |
| 292 | 4'-Me | H | H | 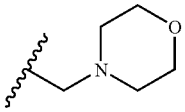 | H | H |
| 293 | 4'-F | H | H | 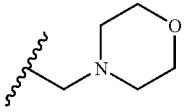 | H | H |
| 294 | 5'-F | H | H | 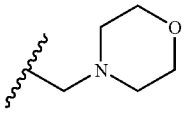 | H | H |

TABLE 1-continued

| Compound # | R¹ | 2 | 3 | 4 | 5 | 6 |
|---|---|---|---|---|---|---|
| 295 | 6'-F | H | H | -CH₂-morpholine | H | H |
| 296 | 4'-Me | H | H | -NH-(CH₂)₃-morpholine | H | H |
| 297 | H | H | H | -NH-(CH₂)₃-morpholine | H | H |
| 298 | 6'-F | H | H | -NH-(CH₂)₃-morpholine | H | H |
| 299 | 5'-Cl | H | H | -NH-(CH₂)₃-morpholine | H | H |
| 300 | 5'-F | H | H | -NH-(CH₂)₃-morpholine | H | H |
| 301 | 4'-F | H | H | -NH-(CH₂)₃-morpholine | H | H |
| 302 | H | H | H | -NH-(CH₂)₃-(4-methylpiperazine) | H | H |
| 303 | 4'-Me | H | H | -NH-(CH₂)₃-(4-methylpiperazine) | H | H |
| 304 | 6'-F | H | H | -NH-(CH₂)₃-(4-methylpiperazine) | H | H |

TABLE 1-continued
| Compound # | R¹ | 2 | 3 | 4 | 5 | 6 |
|---|---|---|---|---|---|---|
| 305 | H | H | H | 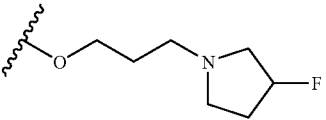 [SMILES: *OCCCN1CCC(F)C1] | H | H |
| 306 | H | H | H | 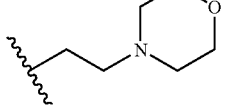 | H | H |
| 307 | 5'-Cl | H | H | 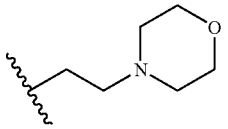 | H | H |
| 308 | 4'-Me | H | H | 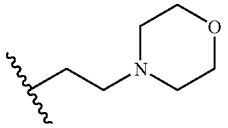 | H | H |
| 309 | 4'-F | H | H | 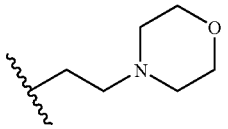 | H | H |
| 310 | 5'-F | H | H | 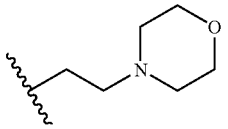 | H | H |
| 311 | 6'-F | H | H | 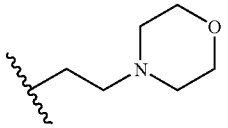 [SMILES: *CCN1CCOCC1] | H | H |
| 312 | H | H | H | 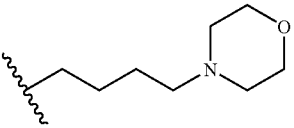 | H | H |
| 313 | 5'-Cl | H | H | 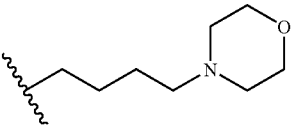 | H | H |
| 314 | 4'-Me | H | H | 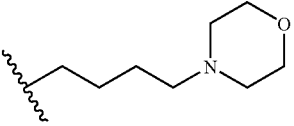 | H | H |
| 315 | 4'-F | H | H | 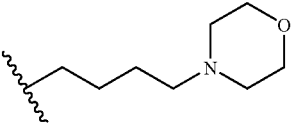 | H | H |

TABLE 1-continued

| Compound # | R¹ | 2 | 3 | 4 | 5 | 6 |
|---|---|---|---|---|---|---|
| 316 | 5'-F | H | H | (4-morpholinyl)butyl | H | H |
| 317 | 6'-F | H | H | (4-morpholinyl)butyl | H | H |
| 318 | H | H | H | (1-piperidinyl)butyl | H | H |
| 319 | 5'-Cl | H | H | (1-piperidinyl)butyl | H | H |
| 320 | 4'-Me | H | H | (1-piperidinyl)butyl | H | H |
| 321 | 4'-F | H | H | (1-piperidinyl)butyl | H | H |
| 322 | 5'-F | H | H | (1-piperidinyl)butyl | H | H |
| 323 | 6'-F | H | H | (1-morpholinyl)butyl | H | H |

The present compositions may also comprise a TKI or a combination of TKIs represented by the following formulas closed in U.S. patent app Ser. Nos. 10/256,879 (U.S. Pub. No. 20030199478) and 10/259,703 (U.S. Pub. No. 20030225152)

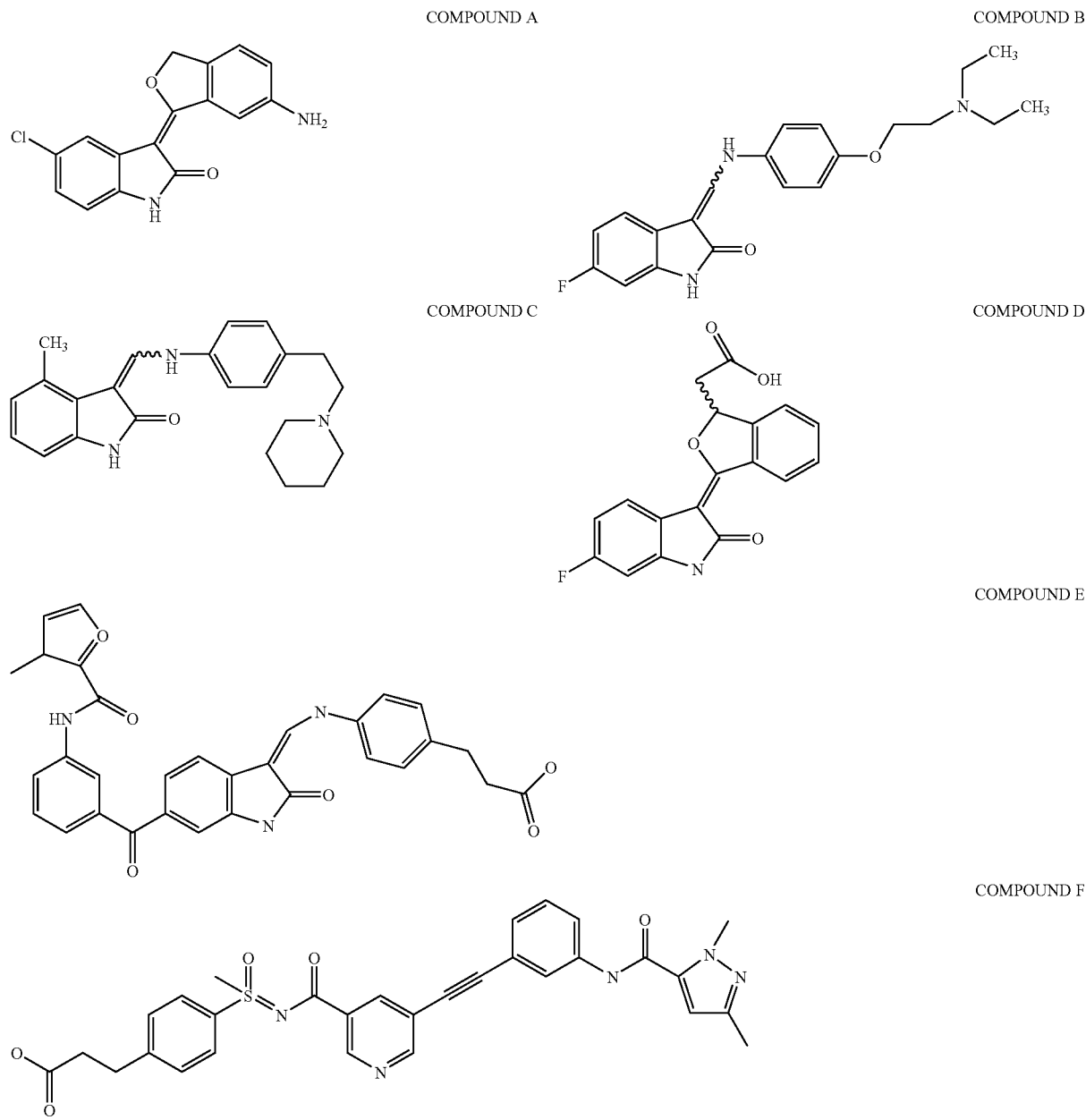

COMPOUND A

COMPOUND B

COMPOUND C

COMPOUND D

COMPOUND E

COMPOUND F

Additional TKIs that may be used in the present implants include those compounds disclosed in Goel et al., "Tyrosine Kinase Inhibitors: A Clinical Perspective", CURRENT ONCOLOGY REPORTS, 4:9-19 (2002); Haluska et al., "Receptor tyrosine kinase inhibitors", CURRENT OPINION IN INVESTIGATIONAL DRUGS, 2(2):280-286 (2001); Hubbard et al., "Protein tyrosine kinase structure and function" ANNU. REV. BIOCHEM., 69:373-98 (2000); Busse et al., "Tyrosine kinase inhibitors: rationale, mechanisms of action, and implications for drug resistance", SEMIN ONCOL 28(suppl 16) 47-55 (2001); and Fabbro et al., "Protein tyrosine kinase inhibitors: new treatment modalities?", CURRENT OPINION IN PHARMACOLOGY, 2:374-381 (2002).

The foregoing compounds may be synthesized using routine chemical technologies and methods including those disclosed and the other above-identified references, all of which are hereby incorporated by reference herein in their entirety.

The present compounds may also include salts of the TKIs. Pharmaceutically acceptable acid addition salts of the compounds of the invention are those formed from acids which form non-toxic addition salts containing pharmaceutically acceptable anions, such as the hydrochloride, hydrobromide, hydroiodide, sulfate, or bisulfate, phosphate or acid phosphate, acetate, maleate, fumarate, oxalate, lactate, tartrate, citrate, gluconate, saccharate and p-toluene sulphonate salts.

Thus, the formulation of the present invention may comprise a TKI component which comprises, consists essentially of, or consists of a TKI, salts thereof, and mixtures thereof.

In certain embodiments, the present invention does not include Compound A. In another embodiment the present invention does not include Compound B. In another embodiment the present invention does not include Compound C. In another embodiment the present invention does not include Compound D. In another embodiment the present invention does not include Compound E. In another embodiment the present invention does not include Compound F. In certain embodiments the present invention does not include two or more compounds selected from the group consisting of Compound A, Compound B, Compound C, Compound D, Compound E and Compound F.

Additional TKIs may be obtained or synthesized using conventional methods, such as by routine chemical synthesis methods known to persons of ordinary skill in the art. Therapeutically effective TKIs may be screened and identified using conventional screening technologies used for the TKIs described herein.

The TKIs may be in a soluble form, or in a particulate or powder form in suspension in the present formulations.

The TKI component of the present formulations is preferably from about 10% to 90% by weight of the compositions. More preferably, the TKI component is from about 20% to about 80% by weight of the composition. In a preferred embodiment, the TKI component comprises about 40% by weight of the composition (e.g., 30%-50%). In another embodiment, the TKI comprises about 60% by weight of the composition. In yet another embodiment of the invention, the TKI component comprises about 0.2 mg per 100 µl or about 0.4 mg per 100 µl, or about 0.5 mg per 100 µl or about 1.0 mg per 100 µl or about 2.0 mg per 100 µl, or about 4.0 mg per 100 µl, or about 5.0 mg per 100 µl, or about 6.0 mg per 100 µl, or about 7.0 mg per 100 µl, or about 8.0 mg per 100 µl, or about 10 mg per 100 µl, or about 20 mg per 100 µl, or about 40 mg per 100 µl, or about 60 mg per 100 µl, or about 80 mg per 100 µl.

In all cases, the present invention is drawn to a composition, or a method of making or using such a composition, comprising a therapeutically effective amount of a TKI component. A "therapeutically effective amount" means an amount or concentration of a TKI component contained in the composition sufficient, when administered to the posterior segment of an eye of an animal or human suffering retinal and/or choriodal angiogenesis, to provide a statistically significant, reproducible reduction in the progression of such angiogenesis, for example, as measured by retinal fluorescein leakage, retinal vessel tortuosity/dilation, and/or BAB (blood aqueous barrier) breakdown, as compared to a control eye of a similarly situated human or animal, given the same volume of an otherwise identical composition lacking the TKI component.

In addition to the TKI(s) included in the present intraocular formulations, the intraocular formulations may also include one or more additional ophthalmically acceptable therapeutic agents. For example, the composition may include one or more antihistamines, one or more antibiotics, one or more beta blockers, one or more steroids, one or more antineoplastic agents, one or more immunosuppressive agents, one or more antiviral agents, one or more antioxidant agents, and mixtures thereof.

Pharmacologic or therapeutic agents which may find use in the present systems, include, without limitation, those disclosed in U.S. Pat. Nos. 4,474,451, columns 4-6 and 4,327,725, columns 7-8.

Examples of antihistamines include, and are not limited to, loradatine, hydroxyzine, diphenhydramine, chlorpheniramine, brompheniramine, cyproheptadine, terfenadine, clemastine, triprolidine, carbinoxamine, diphenylpyraline, phenindamine, azatadine, tripelennamine, dexchlorpheniramine, dexbrompheniramine, methdilazine, and trimprazine doxylamine, pheniramine, pyrilamine, chiorcyclizine, thonzylamine, and derivatives thereof.

Examples of antibiotics include without limitation, cefazolin, cephradine, cefaclor, cephapirin, ceftizoxime, cefoperazone, cefotetan, cefutoxime, cefotaxime, cefadroxil, ceftazidime, cephalexin, cephalothin cefamandole, cefoxitin, cefonicid, ceforanide, ceftriaxone, cefadroxil, cephradine, cefuroxime, cyclosporine, ampicillin, amoxicillin, cyclacillin, ampicillin, penicillin G, penicillin V potassium, piperacillin, oxacillin, bacampicillin, cloxacillin, ticarcillin, azlocillin, carbenicillin, methicillin, nafcillin, erythromycin, tetracycline, doxycycline, minocycline, aztreonam, chloramphenicol, ciprofloxacin hydrochloride, clindamycin, metronidazole, gentamicin, lincomycin, tobramycin, vancomycin, polymyxin B sulfate, colistimethate, colistin, azithromycin, augmentin, sulfamethoxazole, trimethoprim, gatifloxacin, ofloxacin, and derivatives thereof.

Examples of beta blockers include acebutolol, atenolol, labetalol, metoprolol, propranolol, timolol, and derivatives thereof.

Examples of steroids include corticosteroids, such as cortisone, prednisolone, flurometholone, dexamethasone, medrysone, loteprednol, fluazacort, hydrocortisone, prednisone, betamethasone, prednisone, methylprednisolone, riameinolone hexacatonide, paramethasone acetate, diflorasone, fluocinonide, fluocinolone, triamcinolone, derivatives thereof, and mixtures thereof.

Examples of antineoplastic agents include adriamycin, cyclophosphamide, actinomycin, bleomycin, duanorubicin, doxorubicin, epirubicin, mitomycin, methotrexate, fluorouracil, carboplatin, carmustine (BCNU), methyl-CCNU, cisplatin, etoposide, interferons, camptothecin and derivatives thereof, phenesterine, taxol and derivatives thereof, taxotere and derivatives thereof, vinblastine, vincristine, tamoxifen, etoposide, piposulfan, cyclophosphamide, and flutamide, and derivatives thereof.

Examples of immunosuppressive agents include cyclosporine, azathioprine, tacrolimus, and derivatives thereof.

Examples of antiviral agents include interferon gamma, zidovudine, amantadine hydrochloride, ribavirin, acyclovir, valciclovir, dideoxycytidine, phosphonoformic acid, ganciclovir and derivatives thereof.

Examples of antioxidant agents include ascorbate, alpha-tocopherol, mannitol, reduced glutathione, various carotenoids, cysteine, uric acid, taurine, tyrosine, superoxide dismutase, lutein, zeaxanthin, cryotpxanthin, astazanthin, lycopene, N-acetyl-cysteine, carnosine, gamma-glutamyl-cysteine, quercitin, lactoferrin, dihydrolipoic acid, citrate, Ginkgo Biloba extract, tea catechins, bilberry extract, vitamins E or esters of vitamin E, retinyl palmitate, and derivatives thereof.

Other therapeutic agents include squalamine, carbonic anhydrase inhibitors, alpha agonists, prostamides, prostaglandins, antiparasitics, antifungals, and derivatives thereof.

The amount of active agent or agents employed in the implant, individually or in combination, will vary widely depending on the effective dosage required and the desired rate of release from the implant. As indicated herein, the agent will be at least about 1, more usually at least about 10 weight percent of the implant, and usually not more than about 80, more usually not more than about 40 weight percent of the compositions.

The present implants are configured to release an amount of the TKI(s) effective to treat or reduce a symptom of an ocular condition, such as an ocular condition selected from the conditions listed below.

All of the viscous formulations disclosed herein may also be configured to release the antiexcitotoxic agent(s) or additional therapeutic agents, as described above, which to prevent diseases or conditions, such as the following:

Glaucoma maculopathies/retinal degeneration: macular degeneration, including age related macular degeneration (ARMD), such as non-exudative age related macular degeneration and exudative age related macular degeneration, choroidal neovascularization, retinopathy, including diabetic retinopathy, acute and chronic macular neuroretinopathy, central serous chorioretinopathy, and macular edema, including cystoid macular edema, and diabetic macular edema.

Uveitis/retinitis/choroiditis: acute multifocal placoid pigment epitheliopathy, Behcet's disease, birdshot retinochoroidopathy, infectious (syphilis, lyme, tuberculosis, toxoplasmosis), uveitis, including intermediate uveitis (pars planitis) and anterior uveitis, multifocal choroiditis, multiple evanescent white dot syndrome (MEWDS), ocular sarcoidosis, posterior scleritis, serpignous choroiditis, subretinal fibrosis, uveitis syndrome, and Vogt-Koyanagi-Harada syndrome.

Vascular diseases/exudative diseases: retinal arterial occlusive disease, central retinal vein occlusion, disseminated intravascular coagulopathy, branch retinal vein occlusion, hypertensive fundus changes, ocular ischemic syndrome, retinal arterial microaneurysms, Coat's disease, parafoveal telangiectasis, hemi-retinal vein occlusion, papillophlebitis, central retinal artery occlusion, branch retinal artery occlusion, carotid artery disease (CAD), frosted branch angitis, sickle cell retinopathy and other hemoglobinopathies, angioid streaks, familial exudative vitreoretinopathy, Eales disease.

Traumatic/surgical: sympathetic ophthalmic, uveitic retinal disease, retinal detachment, trauma, laser, PDT, photocoagulation, hypoperfusion during surgery, radiation retinopathy, bone marrow transplant retinopathy.

Proliferative disorders: proliferative vitreal retinopathy and epiretinal membranes, proliferative diabetic retinopathy.

Infectious disorders: ocular histoplasmosis, ocular toxocariasis, presumed ocular histoplasmosis syndrome (POHS), endophthalmitis, toxoplasmosis, retinal diseases associated with HIV infection, choroidal disease associated with HIV infection, uveitic disease associated with HIV Infection, viral retinitis, acute retinal necrosis, progressive outer retinal necrosis, fungal retinal diseases, ocular syphilis, ocular tuberculosis, diffuse unilateral subacute neuroretinitis, and myiasis.

Genetic disorders: retinitis pigmentosa, systemic disorders with associated retinal dystrophies, congenital stationary night blindness, cone dystrophies, Stargardt's disease and fundus flavimaculatus, Bests disease, pattern dystrophy of the retinal pigmented epithelium, X-linked retinoschisis, Sorsby's fundus dystrophy, benign concentric maculopathy, Bietti's crystalline dystrophy, pseudoxanthoma elasticum.

Retinal tears/holes: retinal detachment, macular hole, giant retinal tear.

Tumors: retinal disease associated with tumors, congenital hypertrophy of the RPE, posterior uveal melanoma, choroidal hemangioma, choroidal osteoma, choroidal metastasis, combined hamartoma of the retina and retinal pigmented epithelium, retinoblastoma, vasoproliferative tumors of the ocular fundus, retinal astrocytoma, intraocular lymphoid tumors.

Miscellaneous: punctate inner choroidopathy, acute posterior multifocal placoid pigment epitheliopathy, myopic retinal degeneration, acute retinal pigment epithelitis and the like.

In one embodiment, a viscous formulation comprising a TKI component, such as the formulations disclosed herein, is administered to a posterior segment of an eye of a human or animal patient. In at least one embodiment, a viscous TKI-containing formulation of the present invention is administered (e.g., injected, into the subretinal space of the eye. In other embodiments, a method of treating a patient may include placing the TKI containing composition of the present invention directly into the posterior chamber of the eye. In other embodiments, a method of treating a patient may comprise administering the composition to the patient by at least one of intravitreal injection, subconjuctival injection, sub-tenon injections, retrobulbar injection, and suprachoroidal injection.

In at least one embodiment, a method of improving vision or maintaining vision in a patient comprises administering a composition containing one or more TKI component, as disclosed herein to a patient by at least one of intravitreal injection, subconjuctival injection, sub-tenon injection, retrobulbar injection, and suprachoroidal injection. A syringe apparatus including an appropriately sized needle, for example, a 22 gauge needle, a 27 gauge needle or a 30 gauge needle, can be effectively used to inject the composition with the posterior segment of an eye of a human or animal.

In another aspect of the invention, kits for treating an ocular condition of the eye are provided, comprising: a) a container comprising an extended release composition comprising a therapeutic component including a TKI component in a viscous carrier; and b) instructions for use. Such a kit may comprise a pre-loaded syringe ready for injection.

EXAMPLES

The following non-limiting Examples are presented to exemplify aspects of the present invention.

Example 1

Intravitreal Pharmacokinetics of TKIs in Fluid Compositions

The ocular pharmacokinetics of 3 [(4-Morpholin-4-yl-phenylamino)-methylene]-1,3-dihydro-indol-2-one (COMPOUND G), 3-(6-Amino-3H-isobenzofuran-1-ylidene)-5-chloro-1,3-dihydro-indol-2-one (COMPOUND A), COMPOUND H and COMPOUND I following single intravitreal injections into female albino rabbit eyes was determined. The animals were dosed with a 50 mL intravitreal aqueous saline injection of 242 ng COMPOUND H, 128 ng COMPOUND I, 114 ng 3-[(4-Morpholin-4-yl-phenylamino)-methylene]-1,3-dihydro-indol-2-one or 222 ng 3-(6-Amino-3H-isobenzofuran-1-ylidene)-5-chloro-1,3-dihydro-indol-2-one per eye. Vitreous humor samples (n=4 eyes per timepoint) were collected at 0.5, 1, 2, 4, 8, and 12 hr postdose. The TKI concentration in the vitreous humor was determined using a liquid chromatography tandem mass spectrometry method (LC-MS/MS).

As shown in the Table below, all compounds tested were eliminated fairly rapidly from the rabbit eye. This indicates that the TKIs are eliminated by means of a transretinal route of elimination. However, even though elimination was extremely rapid it was determined that local sustained delivery was feasible. Based on the vitreal clearance determined in this study for 3-[(4-Morpholin-4-yl-phenylamino)-methylene]-1,3-dihydro-indol-2-one, 3-(6-Amino-3H-isobenzofuran-1-ylidene)-5-chloro 1,3-dihydro-indol-2-one, COMPOUND H and COMPOUND I, and assuming steady state efficacious concentration at twice the $EC_{50}$ values (determined by in vitro receptor binding and intracellular $Ca^{2+}$ assay), these compounds could be successfully formulated for intraocular delivery. This data is summarized in Table 2 below.

TABLE 2

TKI Pharmacokinetic Parameters after a Single Intravitreal Injection

| Parameter | COMPOUND G | COMPOUND A | COMPOUND H | COMPOUND I |
|---|---|---|---|---|
| Dose (ng) | 114 | 222 | 242 | 128 |
| $C_0$ (ng/mL) | 502 | 566 | 222 | 332 |
| $t_{1/2}$ (hr) | 1.21 | 2.59 | 1.11 | 2.32 |
| $AUC_{0-tlast}$ (ng · hr/mL) | 488 | 778 | 272 | 466 |
| Cl (mL/hr) | 0.232 | 0.260 | 0.885 | 0.270 |
| $V_{ss}$ (mL) | 0.255 | 0.705 | 1.23 | 0.577 |
| Theoretical 6 mo dose | 200 ug | 5 ug | 150 ug | 126 ug |

Examples 2 TO 8

Eight compositions are as follows:

TABLE 3

| Ingredient | Example 1 | Example 2 | Example 3 | Example 4 |
|---|---|---|---|---|
| COMPOUND A | 0.5 mg | | 1 mg | |
| Sodium Hyaluronate (average molecular weight 0.6 × 10⁶ DALTONS) | 0.05% (w/v) | 0.5% (w/v) | 0.05% (w/v) | 0.5% (w/v) |
| Sodium Phosphate | 0.4% (w/v) | 0.4% (w/v) | 0.4% (w/v) | 0.4% (w/v) |
| Vitamin E-TPGS | 0.5% (w/v) | 0.5% (w/v) | 0.0 | 0.0 |
| COMPOUND I | | 0.5 mg (w/v) | | 1 mg |
| Water for Injection | q.s. | q.s. | q.s. | q.s. |
| Viscosity (at 25° C.) at shear rate 0.1/second | 20 cps | 500 cps | 20 cps | 500 cps |

TABLE 4

| Ingredient | Example 5 | Example 6 | Example 7 | Example 8 |
|---|---|---|---|---|
| COMPOUND G | 0.5 mg | | 1 mg | |
| Sodium Hyaluronate (average molecular weight 0.6 × 10⁶ DALTONS) | 0.05% (w/v) | 0.5% (w/v) | 0.05% (w/v) | 0.5% (w/v) |
| Sodium Phosphate | 0.4% (w/v) | 0.4% (w/v) | 0.4% (w/v) | 0.4% (w/v) |
| Vitamin E-TPGS | 0.5% (w/v) | 0.5% (w/v) | 0.0 | 0.0 |
| COMPOUND H | | 0.5 mg | | 1 mg |
| Water for Injection | q.s. | q.s. | q.s. | q.s. |
| Viscosity (at 25° C.) at shear rate 0.1/second | 20 cps | 500 cps | 20 cps | 500 cps |

Each of these compositions is prepared as follows.

A concentrated solution of each TKI is made by combining the TKI with water, and Vitamin E-TPGS. These ingredients are mixed and then autoclaved. The sodium hyaluronate may be purchased as a sterile powder or sterilized by filtering a dilute solution followed by lyophilization to yield a sterile powder. The sterile sodium hyaluronate is dissolved in water to make an aqueous concentrate of at least twice the desired final concentration. Each concentrated TKI solution is mixed and added to the sodium hyaluronate concentrate, with stirring. Water is added q.s. (quantum sufficit, as much as suffices, in this case as much as is required to prepare the concentration of the solution, gel or suspension) and the mixture is then mixed until homogenous.

These compositions can be marketed in small volume pharmaceutical grade glass bottles, and are found to be therapeutically effective as a therapeutic agent for the treatment of diabetic retinopathy when injected intravitreally into human eyes.

Examples 9 TO 11

Three compositions are as follows:

TABLE 5

| Ingredient | Example 9 | Example 10 | Example 11 |
|---|---|---|---|
| COMPOUND E | 0.5 mg | 1.0 mg | 2.0 mg |
| Sodium hyaluronate | 3.0% (w/v) | 2.5% (w/v) | 2.0% (w/v) |
| Sodium Phosphate | 0.4% (w/v) | 0.4% (w/v) | 0.4% (w/v) |
| Water for Injection | q.s. | q.s. | q.s. |
| Viscosity (at 25° C.) at shear rate 0.1/second | 300,000 cps | 180,000 cps | 100,000 cps |

These compositions are prepared in a manner substantially analogous to that set forth in Example 2.

The high viscosities of the compositions substantially slows the diffusion rate of the TKI when administered into the eye such as by intravitreal injection. These compositions can be marketed in prefilled syringes since they can not easily be removed by a needle and syringe from a container. However, with the compositions in prefilled syringes, the compositions can be effectively injected into the posterior segment of an eye of a human using a 27 gauge or a 30 gauge needle to provide a desired therapeutic effect in the human eye.

The compositions of Examples 9 to 11 employ or contain a sufficient concentration of high molecular weight sodium hyaluronate so as to form a gelatinous plug or drug depot upon intravitreal injection into a human eye.

Examples 12 and 13

Two compositions are as follows:

TABLE 3

| Ingredient | Example 12 | Example 13 |
|---|---|---|
| COMPOUND F | 0.5 mg | 1 mg |
| Sodium hyaluronate (polymeric) | 2.5% (w/v) | 2.3% (w/v) |
| Sodium chloride | 0.63% (w/v) | 0.63% (w/v) |
| dibasic sodium phosphate, heptahydrate | 0.30% (w/v) | 0.30% (w/v) |
| Monobasic sodium phosphate, monohydrate | 0.04% (w/v) | 0.04% (w/v) |
| Water for Injection | q.s. | q.s. |
| Viscosity (at 25° C.) at shear rate 0.1/second | 170,000 ± 25% cps | 200,000 ± 25% cps |

These compositions are prepared in a manner substantially analogous to that set forth in Example 2.

These compositions can be marketed in prefilled syringes since they can not easily be removed by a needle and syringe from a container. However, with the compositions in prefilled syringes, the compositions can be effectively injected into the posterior segment of an eye of a human using a 27 gauge or a 30 gauge needle to provide a desired therapeutic effect in the human eye.

The sodium hyaluronate powders used in these compositions (as well as in the other compositions identified in the Examples herein) have water contents in a range of about 4% to about 20%, preferably about 4% to about 8%, by weight. Differences in the average molecular weight of the hyaluronate used can result in variation in the viscosity of compositions in accordance with the present invention such that the compositions have the same nominal chemical make-ups. Thus, the viscosities indicated herein should be understood to be target viscosities, with the composition being acceptable for use if the actual viscosity of the composition is within plus or minus (±) about 25% or about 30% or about 35% of the target viscosity.

Because each of the compositions set forth in the Examples has a density of about 1 gm/ml, the percentages set forth herein as being based on weight per volume (w/v) can also be considered as being based on weight per weight (w/w).

The compositions of Examples 1-13 employ or contain a sufficient concentration of high molecular weight (i.e. polymeric) sodium hyaluronate so as to form a gelatinous plug or drug depot upon intravitreal injection into a human eye. Preferably the average molecular weight of the hyaluronate used is less than about 2 million, and more preferably the average molecular weight of the hyaluronate used is between about 1.3 million and 1.6 million. Since sodium hyaluronate solutions are subject to dramatic shear thinning, these formulations are easily injected through 27 gauge or even 30 gauge needles.

The Example 1-13 formulations can be used to treat, for example, exudative macular degeneration, diabetic retinopathy, macular edema, central retinal vein occlusion, and branch retinal vein occlusion. Notable these formulations are made using only excipients that are ophthalmically acceptable; that is, compatible (i.e. non-toxic) to the eye, particularly to the retina.

Example 14

Treatment of Macular Edema with Intravitreal TKI Composition

A 64 year old obese female patient with symptoms of diabetes presents with vision loss due to macula edema with central retinal vein occlusion and/or branch retinal vein occlusion. She receives intravitreal injection of 1 mg of a high viscosity TKI (polymeric hyaluronate based) solution containing COMPOUND F, such as the Example 13 formulation. Equivalent injections are made every 4 months.

Twelve months after the first injection the patient demonstrates an improved best corrected visual acuity of fifteen or more letters from baseline as determined using the Early Treatment of Diabetic Retinopathy Study (ETDRS) visual acuity chart.

Example 15

Treatment of a Posterior Ocular Condition with Intravitreal TKI Composition

Patients with a posterior ocular condition (such as a macular edema, uveitis, or macular degeneration) can be treated by intravitreal injection of 1 mg or 2 mg of a TKI component in a high viscosity gel (polymeric hyaluronate based) containing COMPOUND E, substantially similar to that of the Example 12 or 13 formulation. Alternately, the formulation can be administered by subconjunctival injection to treat the posterior ocular condition. These patients can demonstrate 3 months or more after injection an improved best corrected visual acuity of fifteen or more letters from baseline as determined using the Early Treatment of Diabetic Retinopathy Study (ETDRS) visual acuity chart.

While this invention has been described with respect to various specific examples and embodiments, it is to be understood that the invention is not limited thereto. Each and every one of the references, articles, publications, patents and applications set forth above is hereby expressly incorporated herein by reference in its entirety.

We claim:

1. A method for treating an ocular condition, the method comprising: administering to the interior of an eye a composition comprising a therapeutically effective amount of a tyrosine kinase inhibitor to a mammal suffering from an ocular condition, wherein the composition also comprises i) a viscosity inducing component in an amount effective to increase the viscosity of the composition to a viscosity at about 25° C. of at least about 70,000 cps at a shear rate of about 0.1/second, and ii) a resuspension component, wherein said viscosity inducing component is injectable into the vitreous of a mammalian eye without permanently diminishing visual acuity, and wherein said resuspension component is selected from the group consisting of Vitamin E tocopheryl polyethylene glycol succinates, Vitamin E tocopheryl polyethylene glycol 1000 succinate (Vitamin E TPGS), Vitamin E tocopheryl polyethylene glycol succinamides, and Vitamin E tocopheryl polyethylene glycol 1000 succinamide (Vitamin E TPGSA).

2. The method of claim 1 wherein said composition comprises a suspension.

3. The method of claim 1 wherein the tyrosine kinase inhibitor comprises an agent selected from the group consisting of a peptide tyrosine kinase inhibitor component, a nucleic acid tyrosine kinase inhibitor component, and a small molecule tyrosine kinase inhibitor component.

4. The method of claim 3 wherein said tyrosine kinase inhibitor comprises a small molecule tyrosine kinase inhibitor component.

5. The method of claim 4 wherein said small molecule tyrosine kinase inhibitor component comprises at least one compound selected from the group consisting of compound 1 to compound 323.

6. The method of claim 4 wherein said small molecule tyrosine kinase inhibitor component comprises at least one compound having a structure selected from the group consisting of:

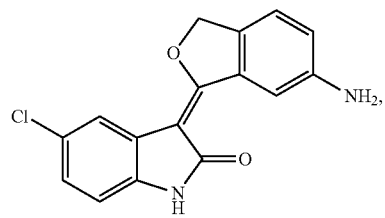
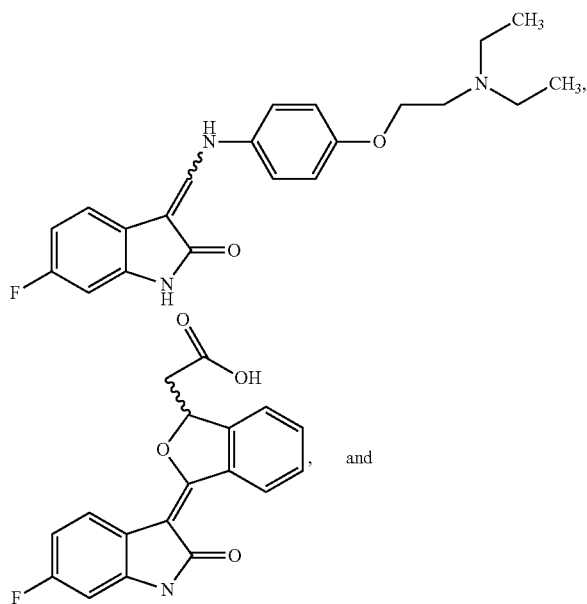
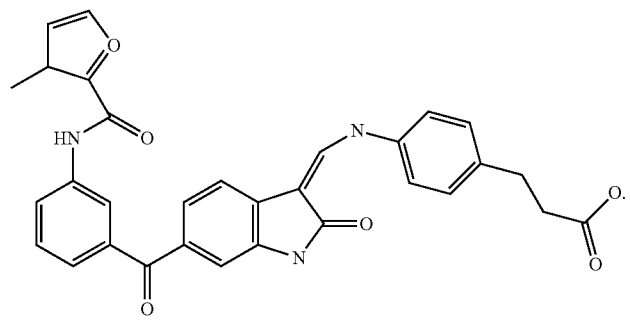
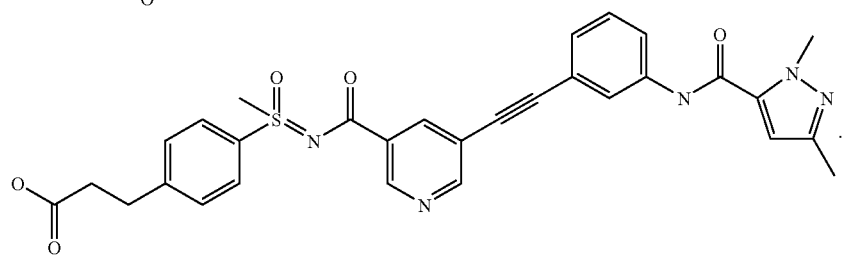
7. The method of claim 6 wherein said small molecule tyrosine kinase inhibitor component has a structure comprising
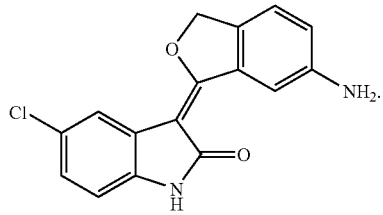 [SMILES: Nc1ccc2c(c1)/C(=C1\C(=O)Nc3ccc(Cl)cc31)OC2]
8. The method of claim 6 wherein said small molecule tyrosine kinase inhibitor component has a structure comprising
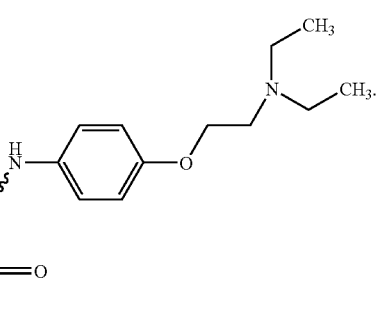
9. The method of claim 6 wherein said small molecule tyrosine kinase inhibitor component has a structure comprising

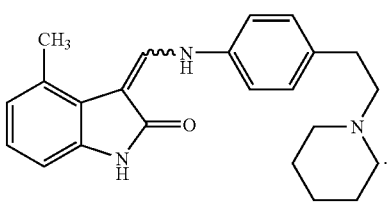 [SMILES: Cc1cccc2c1C(=CNc1ccc(CCN3CCCCC3)cc1)C(=O)N2]

10. The method of claim 6 wherein said small molecule tyrosine kinase inhibitor component has a structure comprising

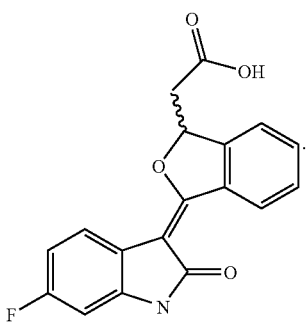 [SMILES: O=C(O)CC1O/C(=C2/C(=O)Nc3cc(F)ccc32)c2ccccc21]

11. The method of claim 6 wherein said small molecule tyrosine kinase inhibitor component has a structure comprising

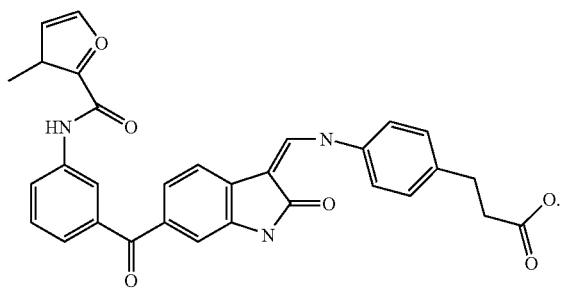

12. The method of claim 1 wherein said viscosity inducing component comprises a compound selected from the group consisting of a hyaluronic acid, and a crosslinked hyaluronate polymer.

13. The method of claim 1 wherein said viscosity inducing component comprises a compound having a molecular weight in the range from about 10,000 Daltons to about 2 million Daltons.

14. The method of claim 13 wherein said viscosity inducing component comprises a compound having a molecular weight in the range of about 100,000 Daltons to about 1.5 million Daltons.

15. The method of claim 13 wherein said viscosity inducing component comprises a compound having a molecular weight in the range of about 200,000 Daltons to about 1 million Daltons.

16. The method of claim 1 wherein said viscosity inducing component has a viscosity of at least about 250,000 cps at a shear rate of 0.1/second.

17. The method of claim 1 wherein said viscosity inducing component has a viscosity of at least about 300,000 cps at a shear rate of 0.1/second.

18. The method of claim 1 wherein said composition is administered to the interior of said eye by placement into the posterior segment of the eye through a 28-gauge needle.

19. The method of claim 1 wherein said composition is administered to the interior of said eye by placement into the posterior segment of the eye through a 30-gauge needle.

20. The method of claim 1 wherein said condition comprises a condition of the posterior segment of the eye.

21. The method of claim 1 wherein said condition is selected from the group consisting of macular degeneration, including non-exudative age related macular degeneration and exudative age related macular degeneration, choroidal neovascularization, retinopathy, diabetic retinopathy, acute and chronic macular neuroretinopathy, central serous chorioretinopathy, macular edema, acute multifocal placoid pigment epitheliopathy, Behcet's disease, birdshot retinochoroidopathy, posterior scleritis, serpignous choroiditis, subretinal fibrosis, uveitis syndrome, Vogt-Koyanagi-Harada syndrome, retinal arterial occlusive disease, central retinal vein occlusion, disseminated intravascular coagulopathy, branch retinal vein occlusion, hypertensive fundus changes, ocular ischemic syndrome, retinal arterial microaneurysms, Coat's disease, parafoveal telangiectasis, hemi-retinal vein occlusion, papillophlebitis, central retinal artery occlusion, branch retinal artery occlusion, carotid artery disease (CAD), frosted branch angitis, sickle cell retinopathy, angioid streaks, familial exudative vitreoretinopathy, Eales disease, proliferative vitreal retinopathy, proliferative diabetic retinopathy, retinal disease associated with tumors, congenital hypertrophy of the RPE, posterior uveal melanoma, choroidal hemangioma, choroidal osteoma, choroidal metastasis, combined hamartoma of the retina and retinal pigmented epithelium, retinoblastoma, vasoproliferative tumors of the ocular fundus, retinal astrocytoma, intraocular lymphoid tumors, myopic retinal degeneration, acute retinal pigment epithelitis.

22. The method of claim 4 wherein said condition is selected from the group consisting of macular degeneration, including non-exudative age related macular degeneration and exudative age related macular degeneration, choroidal neovascularization, retinopathy, diabetic retinopathy, acute and chronic macular neuroretinopathy, central serous chorioretinopathy, macular edema, acute multifocal placoid pigment epitheliopathy, Behcet's disease, birdshot retinochoroidopathy, posterior scleritis, serpignous choroiditis, subretinal fibrosis, uveitis syndrome, Vogt-Koyanagi-Harada syndrome, retinal arterial occlusive disease, central retinal vein occlusion, disseminated intravascular coagulopathy, branch retinal vein occlusion, hypertensive fundus changes, ocular ischemic syndrome, retinal arterial microaneurysms, Coat's disease, parafoveal telangiectasis, hemi-retinal vein occlusion, papillophlebitis, central retinal artery occlusion, branch retinal artery occlusion, carotid artery disease (CAD), frosted branch angitis, sickle cell retinopathy, angioid streaks, familial exudative vitreoretinopathy, Eales disease, proliferative vitreal retinopathy, proliferative diabetic retinopathy, retinal disease associated with tumors, congenital hypertrophy of the RPE, posterior uveal melanoma, choroidal hemangioma, choroidal osteoma, choroidal metastasis, combined hamartoma of the retina and retinal pigmented epithelium, retinoblastoma, vasoproliferative tumors of the ocular fundus, retinal astrocytoma, intraocular lymphoid tumors, myopic retinal degeneration, acute retinal pigment epithelitis.

23. The method of claim 5 wherein said condition is selected from the group consisting of macular degeneration, including non-exudative age related macular degeneration and exudative age related macular degeneration, choroidal neovascularization, retinopathy, diabetic retinopathy, acute and chronic macular neuroretinopathy, central serous chorioretinopathy, macular edema, acute multifocal placoid pigment epitheliopathy, Behcet's disease, birdshot retinochoroidopathy, posterior scleritis, serpignous choroiditis, subretinal fibrosis, uveitis syndrome, Vogt-Koyanagi-Harada syndrome, retinal arterial occlusive disease, central retinal vein occlusion, disseminated intravascular coagulopathy, branch retinal vein occlusion, hypertensive fundus changes, ocular ischemic syndrome, retinal arterial microaneurysms, Coat's disease, parafoveal telangiectasis, hemi-retinal vein occlusion, papillophlebitis, central retinal artery occlusion, branch retinal artery occlusion, carotid artery disease (CAD), frosted branch angitis, sickle cell retinopathy, angioid streaks, familial exudative vitreoretinopathy, Eales disease, proliferative vitreal retinopathy, proliferative diabetic retinopathy, retinal disease associated with tumors, congenital hypertrophy of the RPE, posterior uveal melanoma, choroidal hemangioma, choroidal osteoma, choroidal metastasis, combined hamartoma of the retina and retinal pigmented epithelium, retinoblastoma, vasoproliferative tumors of the ocular fundus, retinal astrocytoma, intraocular lymphoid tumors, myopic retinal degeneration, acute retinal pigment epithelitis.

24. The method of claim 6 wherein said condition is selected from the group consisting of macular degeneration, including non-exudative age related macular degeneration and exudative age related macular degeneration, choroidal neovascularization, retinopathy, diabetic retinopathy, acute and chronic macular neuroretinopathy, central serous chorioretinopathy, macular edema, acute multifocal placoid pigment epitheliopathy, Behcet's disease, birdshot retinochoroidopathy, posterior scleritis, serpignous choroiditis, subretinal fibrosis, uveitis syndrome, Vogt-Koyanagi-Harada syndrome, retinal arterial occlusive disease, central retinal vein occlusion, disseminated intravascular coagulopathy, branch retinal vein occlusion, hypertensive fundus changes, ocular ischemic syndrome, retinal arterial microaneurysms, Coat's disease, parafoveal telangiectasis, hemi-retinal vein occlusion, papillophlebitis, central retinal artery occlusion, branch retinal artery occlusion, carotid artery disease (CAD), frosted branch angitis, sickle cell retinopathy, angioid streaks, familial exudative vitreoretinopathy, Eales disease, proliferative vitreal retinopathy, proliferative diabetic retinopathy, retinal disease associated with tumors, congenital hypertrophy of the RPE, posterior uveal melanoma, choroidal hemangioma, choroidal osteoma, choroidal metastasis, combined hamartoma of the retina and retinal pigmented epithelium, retinoblastoma, vasoproliferative tumors of the ocular fundus, retinal astrocytoma, intraocular lymphoid tumors, myopic retinal degeneration, acute retinal pigment epithelitis.

\* \* \* \* \*